US006258086B1

(12) United States Patent
Ashley et al.

(10) Patent No.: US 6,258,086 B1
(45) Date of Patent: Jul. 10, 2001

(54) CATHETER FOR DELIVERY OF ENERGY TO A SURGICAL SITE

(75) Inventors: John E. Ashley, San Francisco; Hugh R. Sharkey, Woodside; Joel Saal; Jeff A. Saal, both of Portola Valley, all of CA (US)

(73) Assignee: Oratec Interventions, Inc., Menlo Park, CA (US)

(*) Notice: Subject to any disclaimer, the term of this patent is extended or adjusted under 35 U.S.C. 154(b) by 0 days.

(21) Appl. No.: 09/272,806

(22) Filed: Mar. 19, 1999

Related U.S. Application Data

(63) Continuation-in-part of application No. 08/881,527, filed on Jun. 24, 1997, now Pat. No. 5,980,504, and a continuation-in-part of application No. 08/881,525, filed on Jun. 24, 1997, now Pat. No. 6,122,549, and a continuation-in-part of application No. 08/881,692, filed on Jun. 24, 1997, now Pat. No. 6,073,051, and a continuation-in-part of application No. 08/881,693, filed on Jun. 24, 1997, now Pat. No. 6,007,570, and a continuation-in-part of application No. 08/881,694, filed on Jun. 24, 1997, now Pat. No. 6,095,149.

(60) Provisional application No. 60/047,820, filed on May 28, 1997, provisional application No. 60/047,841, filed on May 28, 1997, provisional application No. 60/047,818, filed on May 28, 1997, provisional application No. 60/047,848, filed on May 28, 1997, provisional application No. 60/045,941, filed on May 8, 1997, provisional application No. 60/029,734, filed on Oct. 23, 1996, provisional application No. 60/029,735, filed on Oct. 23, 1996, provisional application No. 60/029,600, filed on Oct. 23, 1996, provisional application No. 60/029,602, filed on Oct. 23, 1996, provisional application No. 08/881,525, filed on Oct. 23, 1996, provisional application No. 08/881,692, filed on Oct. 23, 1996, provisional application No. 08/881,693, filed on Oct. 23, 1996, provisional application No. 08/881,694, filed on Oct. 23, 1996, provisional application No. 60/045,941, filed on Oct. 23, 1996, provisional application No. 60/029,734, filed on Oct. 23, 1996, and provisional application No. 60/078,545, filed on Mar. 19, 1998.

(51) Int. Cl.$^7$ .................................................. A61B 18/18

(52) U.S. Cl. ........................... 606/41; 606/46; 604/510; 604/531; 607/117

(58) Field of Search ............................ 606/27, 41–50; 607/117, 118, 122; 600/585; 604/95.05, 528, 530, 531, 510

(56) References Cited

U.S. PATENT DOCUMENTS

| 4,846,175 | 7/1989 | Frimberger . |
|---|---|---|
| 5,114,402 | 5/1992 | McCoy . |
| 5,152,748 | 10/1992 | Chastagner . |

(List continued on next page.)

FOREIGN PATENT DOCUMENTS

| 39 18316 | 3/1990 | (DE) . |
|---|---|---|
| 0 682 910 A1 | 11/1995 | (EP) . |
| 0 737 487 A2 | 10/1996 | (EP) . |
| 2 645 008 | 10/1990 | (FR) . |
| WO 82/02488 | 8/1982 | (WO) . |
| WO 92/05828 | 4/1992 | (WO) . |

(List continued on next page.)

Primary Examiner—Lee Cohen
Assistant Examiner—David M. Ruddy
(74) Attorney, Agent, or Firm—David J. Weitz; Wilson Sonsini Goodrich & Rosati

(57) ABSTRACT

A catheter for delivering energy to a surgical site is disclosed. The catheter includes at a proximal end a handle and at a distal end a probe. The catheter includes at least one energy delivery device and an activation element. The at least one energy delivery device is located at the distal end of the catheter to deliver energy to portions of the surgical site. The activation element is located at the distal end of the catheter, to transition the probe from a linear to a multi-dimensional shape, within the surgical site. Methods for deploying the probe from the linear to multi-dimensional shape are disclosed.

20 Claims, 15 Drawing Sheets

U.S. PATENT DOCUMENTS

| | | |
|---|---|---|
| 5,279,559 | 1/1994 | Barr . |
| 5,364,395 | 11/1994 | West, Jr. . |
| 5,415,633 | 5/1995 | Lazarus et al. . |
| 5,433,739 * | 7/1995 | Sluijter et al. ............... 607/99 |
| 5,836,947 * | 11/1998 | Fleischman et al. ............ 606/47 |
| 5,882,346 * | 3/1999 | Pomeranz et al. ............ 607/122 |
| 5,980,504 * | 11/1999 | Sharkey et al. ............ 604/510 |
| 5,993,424 * | 11/1999 | Lorenzo et al. ............ 604/164 |
| 6,014,579 * | 1/2000 | Pomeranz et al. ............ 600/374 |
| 6,033,397 * | 3/2000 | Laufer et al. ............... 606/27 |
| 6,056,744 * | 5/2000 | Edwards ............... 606/41 |

FOREIGN PATENT DOCUMENTS

| | | |
|---|---|---|
| WO 93/16648 | 9/1993 | (WO) . |
| WO 95/10981 | 4/1995 | (WO) . |
| WO 95/25471 | 9/1995 | (WO) . |
| WO 96/11638 | 4/1996 | (WO) . |
| WO 96/32885 | 10/1996 | (WO) . |
| WO 96/34559 | 11/1996 | (WO) . |
| WO 98/17190 | 4/1998 | (WO) . |

* cited by examiner

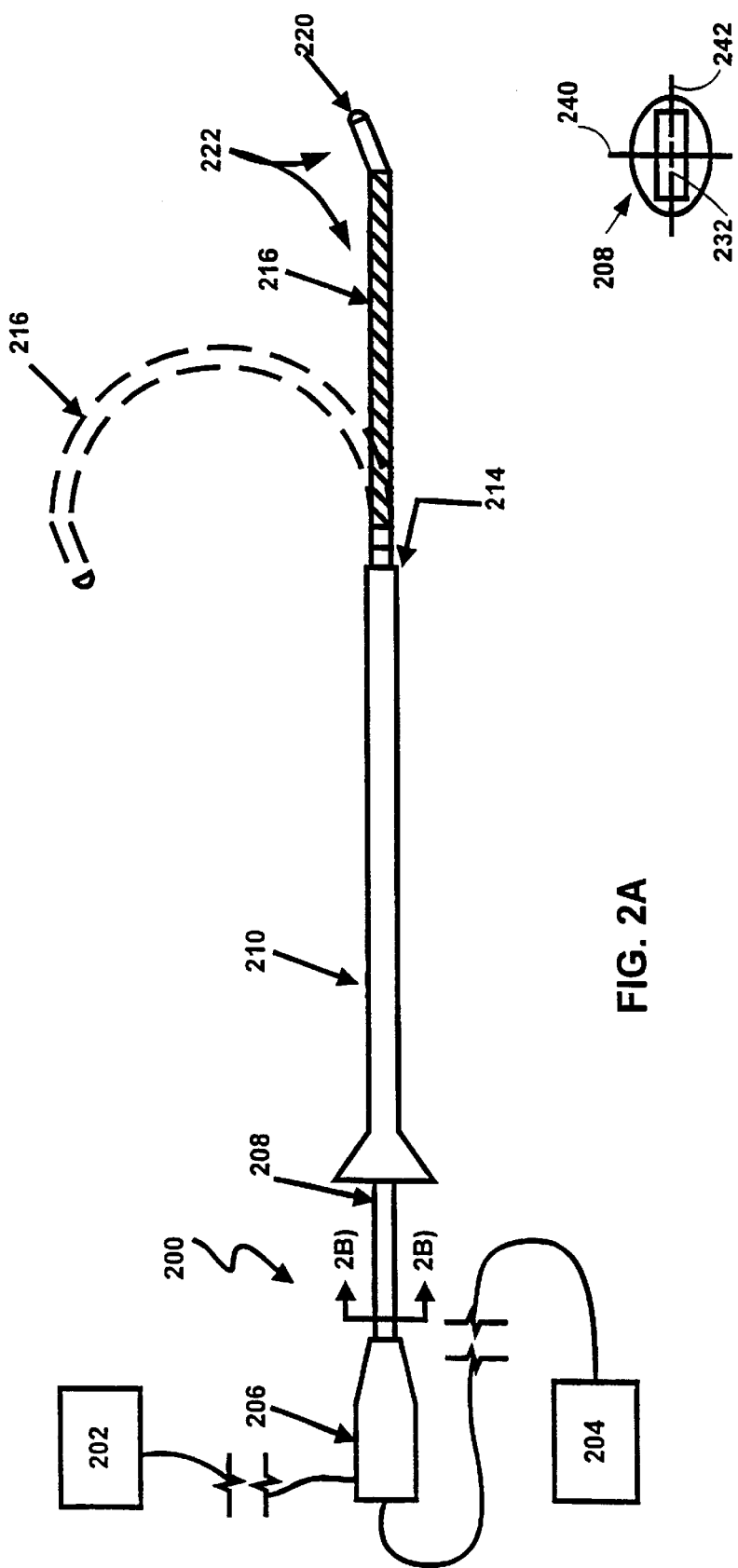
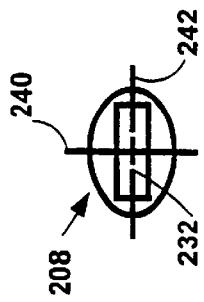
FIG. 2A
FIG. 2B

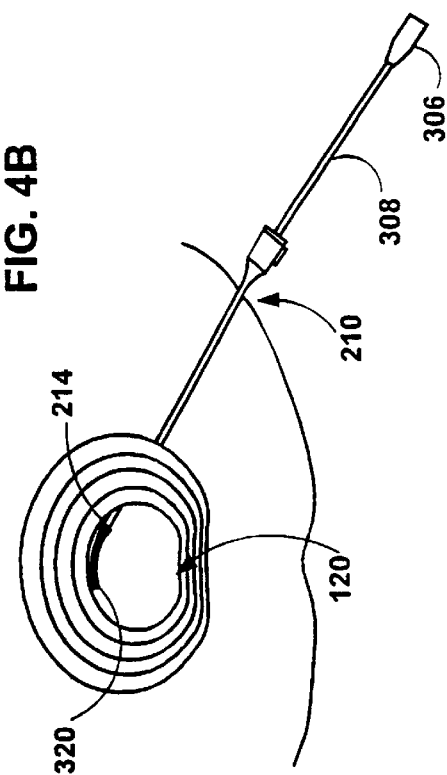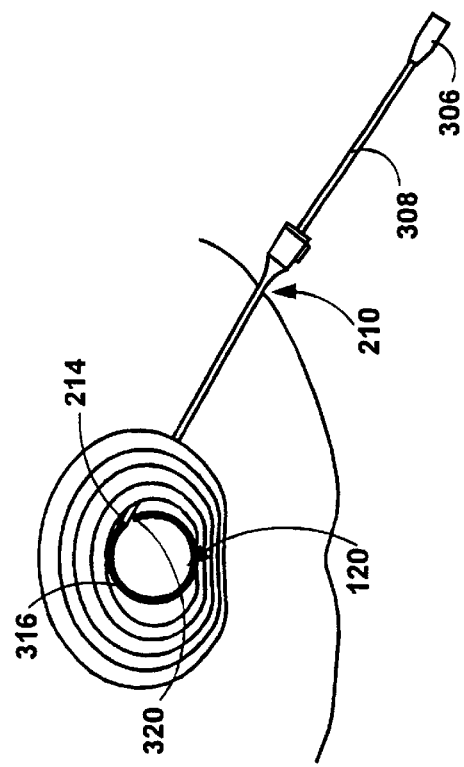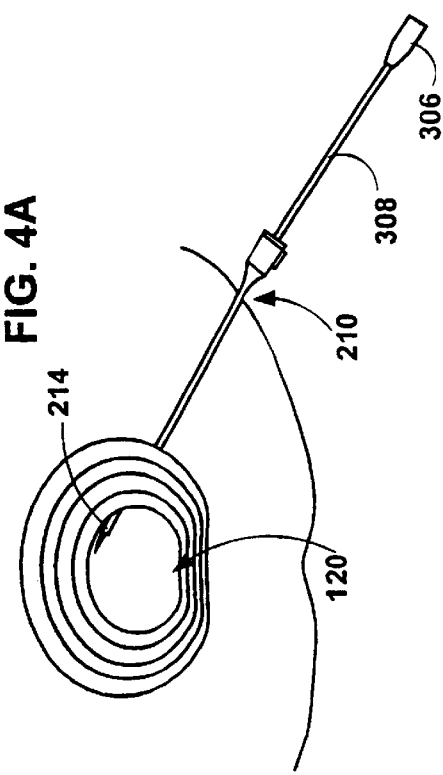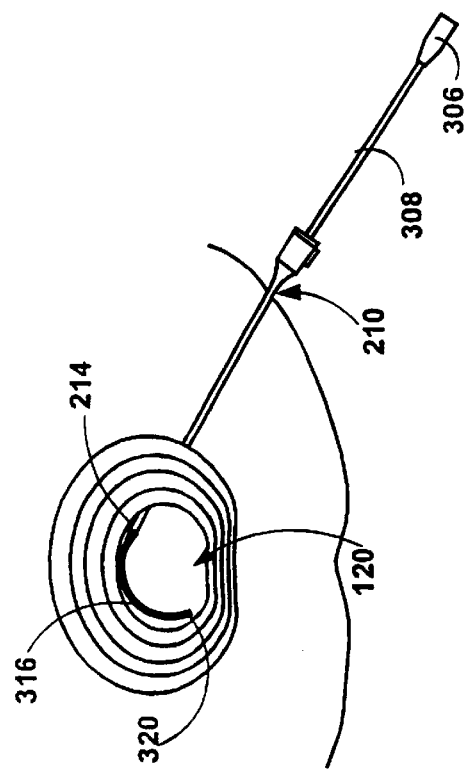

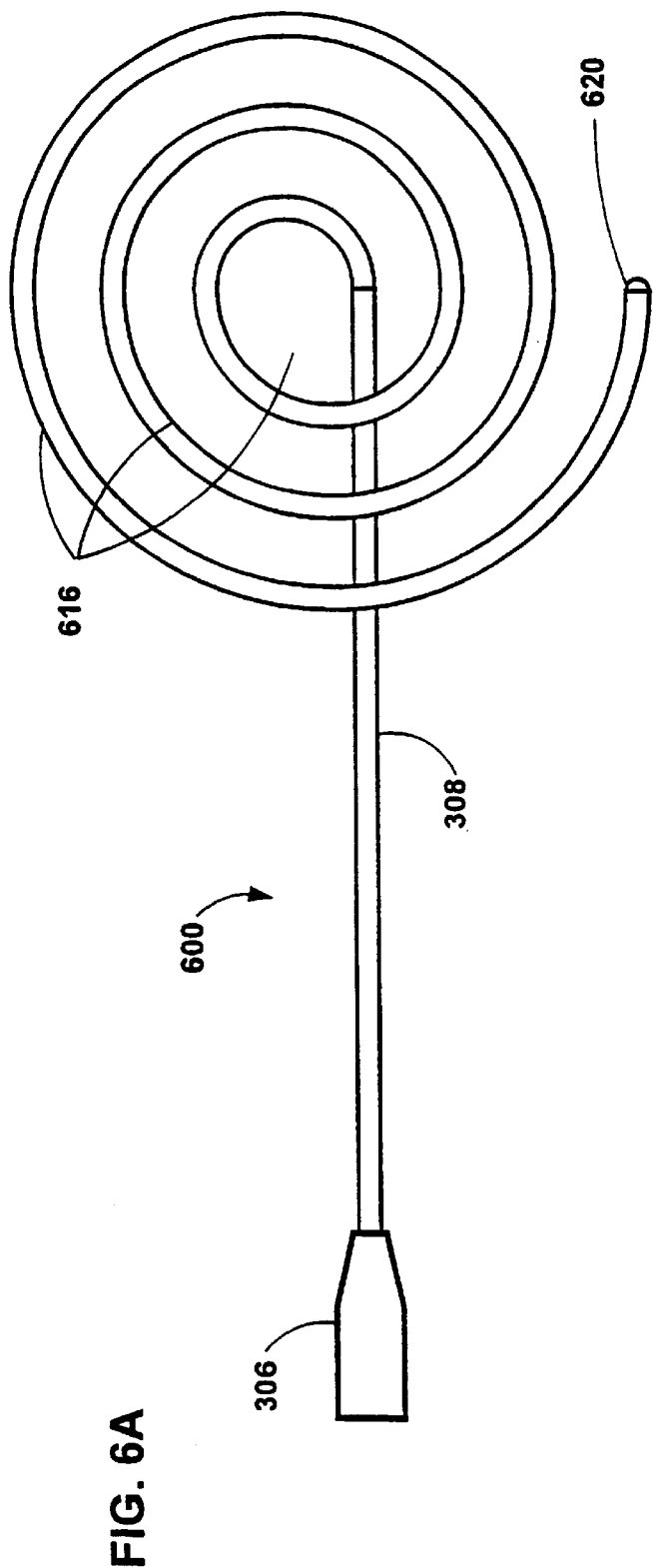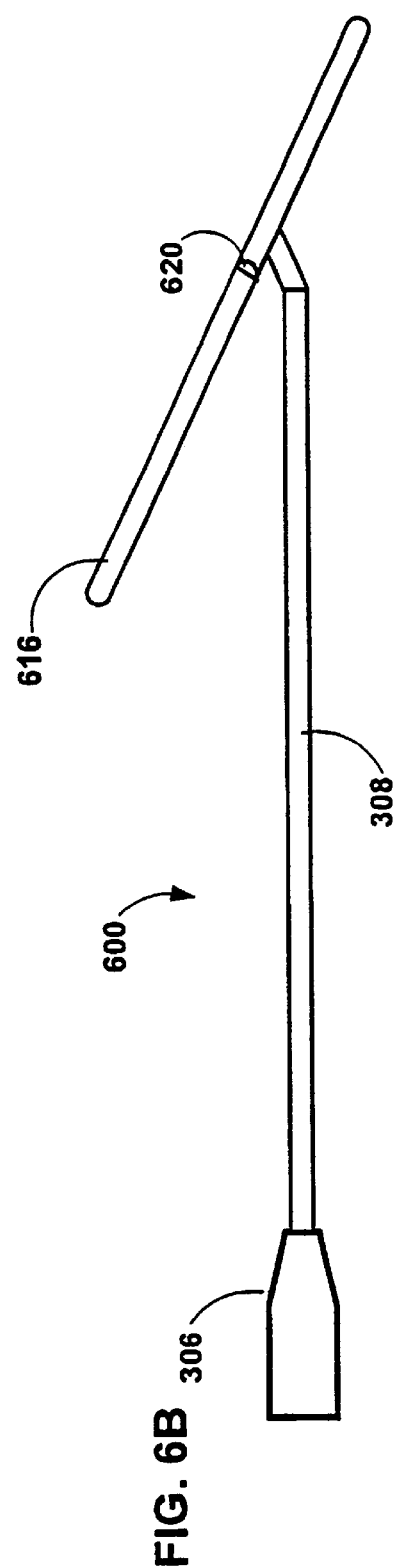
FIG. 6A
FIG. 6B

US 6,258,086 B1

CATHETER FOR DELIVERY OF ENERGY TO A SURGICAL SITE

REFERENCE TO CO-PENDING APPLICATIONS

This application is a continuation in part of provisional application Ser. No. 60/078,545 filed on Mar. 19, 1998 and entitled "Catheter for delivery of energy to a tissue" which is hereby incorporated by reference as if fully set forth herein This application is also a continuation-in-part of U.S. application Ser. Nos. 08/881,527 (now U.S. Pat. No. 5,980, 504), No. 08/881,525 (now U.S. Pat. No. 6,122,549), No. 08/881,692 (now U.S. Pat. No. 6,073,051), No. 08/881,693 (now U.S. Pat. No. 6,007,570), and No. 08/881,694 (now U.S. Pat. No. 6,095,149), each filed Jun. 24, 1997, which each claims priority to U.S. Provisional Application Nos. 60/047,820, 60/047,841, 60/047,818, 60/047,848 each filed May 28, 1997, U.S. Provisional Application No. 60/045,941 filed May 8, 1997 and U.S. Provisional Application Nos. 60/029,734, 60/029,735, 60/029,600, 60/029,602 each filed Oct. 23, 1996. Application Ser. Nos. 08/881,525, 08/881, 692, 08/881,693, 08/881,694, 60/045,941, 60/029,734 are each incorporated herein by reference as if fully set forth herein.

BACKGROUND

1. Field of the Invention

This invention relates to methods and apparatuses to treat intervertebral disc problems and/or for modifying intervertebral disc tissue. More particularly this invention relates to percutaneous techniques to avoid major surgical intervention. In one embodiment, annular fissures are treated by radio frequency (RF) heating of intervertebral disc tissue.

2. Description of Related Art

Intervertebral disc abnormalities (e.g., morphologic) have a high incidence in the population and may result in pain and discomfort if they impinge on or irritate nerves. Disc abnormalities may be the result of trauma, repetitive use, metabolic disorders and the aging process and include such disorders but are not limited to degenerative discs (i) localized tears or fissures in the annulus fibrosus, (ii) localized disc herniations with contained or escaped extrusions, and (iii) chronic, circumferential bulging disc.

Disc fissures occur rather easily after structural degeneration (a part of the aging process that may be accelerated by trauma) of fibrous components of the annulus fibrosus. Sneezing, bending or just attrition can tear these degenerated annulus fibers, creating a fissure. The fissure may or may not be accompanied by extrusion of nucleus pulposus material into or beyond the annulus fibrosus. The fissure itself may be the sole morphological change, above and beyond generalized degenerative changes in the connective tissue of the disc. Even if there is no visible extrusion, biochemicals within the disc may still irritate surrounding structures. Disc fissures can be debilitatingly painful. Initial treatment is symptomatic, including bed rest, pain killers and muscle relaxants. More recently spinal fusion with cages has been performed when conservative treatment did not relieve the pain. The fissure may also be associated with a herniation of that portion of the annulus.

With a contained disc herniation, there are no free nucleus fragments in the spinal canal. Nevertheless, even a contained disc herniation is problematic because the outward protrusion can press on the spinal nerves or irritate other structures. In addition to nerve root compression, escaped nucleus pulposus contents may chemically irritate neural structures. Current treatment methods include reduction of pressure on the annulus by removing some of the interior nucleus pulposus material by percutaneous nuclectomy. However, complications include disc space infection, nerve root injury, hematoma formation, instability of the adjacent vertebrae and collapse of the disc from decrease in height.

Another disc problem occurs when the disc bulges outward circumferentially in all directions and not just in one location. Over time, the disc weakens and takes on a "roll" shape or circumferential bulge. Mechanical stiffness of the joint is reduced and the joint may become unstable. One vertebra may settle on top of another. This problem continues as the body ages, and accounts for shortened stature in old age. With the increasing life expectancy of the population, such degenerative disc disease and impairment of nerve function are becoming major public health problems. As the disc "roll" extends beyond the normal circumference, the disc height may be compromised, and foramina with nerve roots are compressed. In addition, osteophytes may form on the outer surface of the disc roll and further encroach on the spinal canal and foramina through which nerves pass. This condition is called lumbar spondylosis.

It has been thought that such disc degeneration creates segmental instability which disturbs sensitive structures which in turn register pain. Traditional, conservative methods of treatment include bed rest, pain medication, physical therapy or steroid injection. Upon failure of conservative therapy, spinal pain (assumed to be due to instability) has been treated by spinal fusion, with or without instrumentation, which causes the vertebrae above and below the disc to grow solidly together and form a single, solid piece of bone. The procedure is carried out with or without discectomy. Other treatments include discectomy alone or disc decompression with or without fusion.

Nuclectomy can be performed by removing some of the nucleus to reduce pressure on the annulus. However, complications include disc space infection, nerve root injury, hematoma formation, and instability of adjacent vertebrae.

These interventions have been problematic in that alleviation of back pain is unpredictable even if surgery appears successful. In attempts to overcome these difficulties, new fixation devices have been introduced to the market, including but not limited to pedicle screws and interbody fusion cages. Although pedicle screws provide a high fusion success rate, there is still no direct correlation between fusion success and patient improvement in function and pain. Studies on fusion have demonstrated success rates of between 50% and 67% for pain improvement, and a significant number of patients have more pain postoperatively. Therefore, different methods of helping patients with degenerative disc problems need to be explored.

FIGS. 1A and 1B illustrate a cross-sectional anatomical view of a vertebra and associated disc and a lateral view of a portion of a lumbar and thoracic spine, respectively. Structures of a typical cervical vertebra (superior aspect) are shown in FIG. 1A: 104—lamina; 106—spinal cord; 108—dorsal root of spinal nerve; 114—ventral root of spinal nerve; 116—posterior longitudinal ligament; 118—intervertebral disc; 120—nucleus pulposus; 122—annulus fibrosus; 124—anterior longitudinal ligament; 126—vertebral body; 128—pedicle; 130—vertebral artery; 132—vertebral veins; 134—superior articular facet; 136—posterior lateral portion of the annulus; 138—posterior medial portion of the annulus; and 142—spinous process. In FIG. 1A, one side of the intervertebral disc 118 is not shown so that the anterior vertebral body 126 can be seen. FIG. 1B is a lateral aspect of the lower portion of a typical spinal column showing the entire lumbar region and part of the thoracic region and displaying the following structures: 118—intervertebral disc; 126—vertebral body; 142—spinous process; 170—inferior vertebral notch; 172—spinal nerve; 174—superior articular process; 176—lumbar curvature; and 180—sacrum.

The presence of the spinal cord (nerve sac) and the posterior portion of the vertebral body 126, including the spinous process 142, and superior and inferior articular processes 110, prohibit introduction of a needle or trocar from a directly posterior position. This is important because the posterior disc wall is the site of symptomatic annulus tears and disc protrusions/extrusions that compress or irritate spinal nerves for most degenerative disc syndromes. The inferior articular process, along with the pedicle 128 and the lumbar spinal nerve, form a small "triangular" window 168 (shown in black in FIG. 1C) through which introduction can be achieved from the posterior lateral approach. FIG. 1D looks down on an instrument introduced by the posterior lateral approach. It is well known to those skilled in the art that percutaneous access to the disc is achieved by placing an introducer into the disc from this posterior lateral approach, but the triangular window does not allow much room to maneuver. Once the introducer pierces the tough annulus fibrosus, the introducer is fixed at two points along its length and has very little freedom of movement. Thus, this approach has allowed access only to small central and anterior portions of the nucleus pulposus. Current methods do not permit percutaneous access to the posterior half of the nucleus or to the posterior wall of the disc. Major and potentially dangerous surgery is required to access these areas.

U.S. Pat. No. 5,433,739 (the "'739 patent") discloses placement of an RF electrode in an interior region of the disc approximately at the center of the disc. RF power is applied, and heat then putatively spreads out globally throughout the disc. The '739 patent teaches the use of a rigid shaft which includes a sharpened distal end that penetrates through the annulus fibrosus and into the nucleus pulposus. In one embodiment the shaft has to be rigid enough to permit the distal end of the RF electrode to pierce the annulus fibrosus, and the ability to maneuver its distal end within the nucleus pulposus is limited. In another embodiment, a somewhat more flexible shaft is disclosed. However, neither embodiment of the devices of the '739 patent permits access to the posterior, posterior lateral and posterior medial region of the disc, nor do they provide for focal delivery of therapy to a selected local region within the disc or precise temperature control at the annulus. The '739 patent teaches the relief of pain by globally heating the disc. There is no disclosure of treating an annular tear or fissure.

U.S. Pat. No. 5,201,729 (the "'729 patent") discloses the use of an optical fiber that is introduced into a nucleus pulposus. In the '729 patent, the distal end of a stiff optical fiber shaft extends in a lateral direction relative to a longitudinal axis of an introducer. This prevents delivery of coherent energy into the nucleus pulposus in the direction of the longitudinal axis of the introducer. Due to the constrained access from the posterior lateral approach, stiff shaft and lateral energy delivery, the device of the '729 patent is unable to gain close proximity to selected portion(s) of the annulus (i.e., posterior, posterior medial and central posterior) requiring treatment or to precisely control the temperature at the annulus. No use in treating an annular fissure is disclosed.

BRIEF DESCRIPTION OF THE DRAWINGS

A clear conception of the advantages and features constituting the present invention, and of the components and operation of model systems provided with the present invention, will become more readily apparent by referring to the exemplary, and therefore nonlimiting, embodiments illustrated in the drawings accompanying and forming a part of this specification, wherein like reference numerals (if they occur in more than one view) designate the same elements. It should be noted that the features illustrated in the drawings are not necessarily drawn to scale.

FIG. 2A is a plan view of an introducer and an instrument of the invention in which solid lines illustrate the position of the instrument in the absence of bending forces and dotted lines indicate the position the distal portion of the instrument would assume under bending forces applied to the intradiscal section of the instrument, representing an embodiment of the present invention.

FIG. 2B is an end view of the handle of the embodiment shown in FIG. 2A.

FIGS. 4A–D show the surgical steps connected with the insertion of the catheter of FIG. 3 into a surgical site.

FIGS. 6A–6B is a side view of a catheter with a elastically deformed end section with an outward spiral shape.

SUMMARY OF THE INVENTION

Figure 1A:
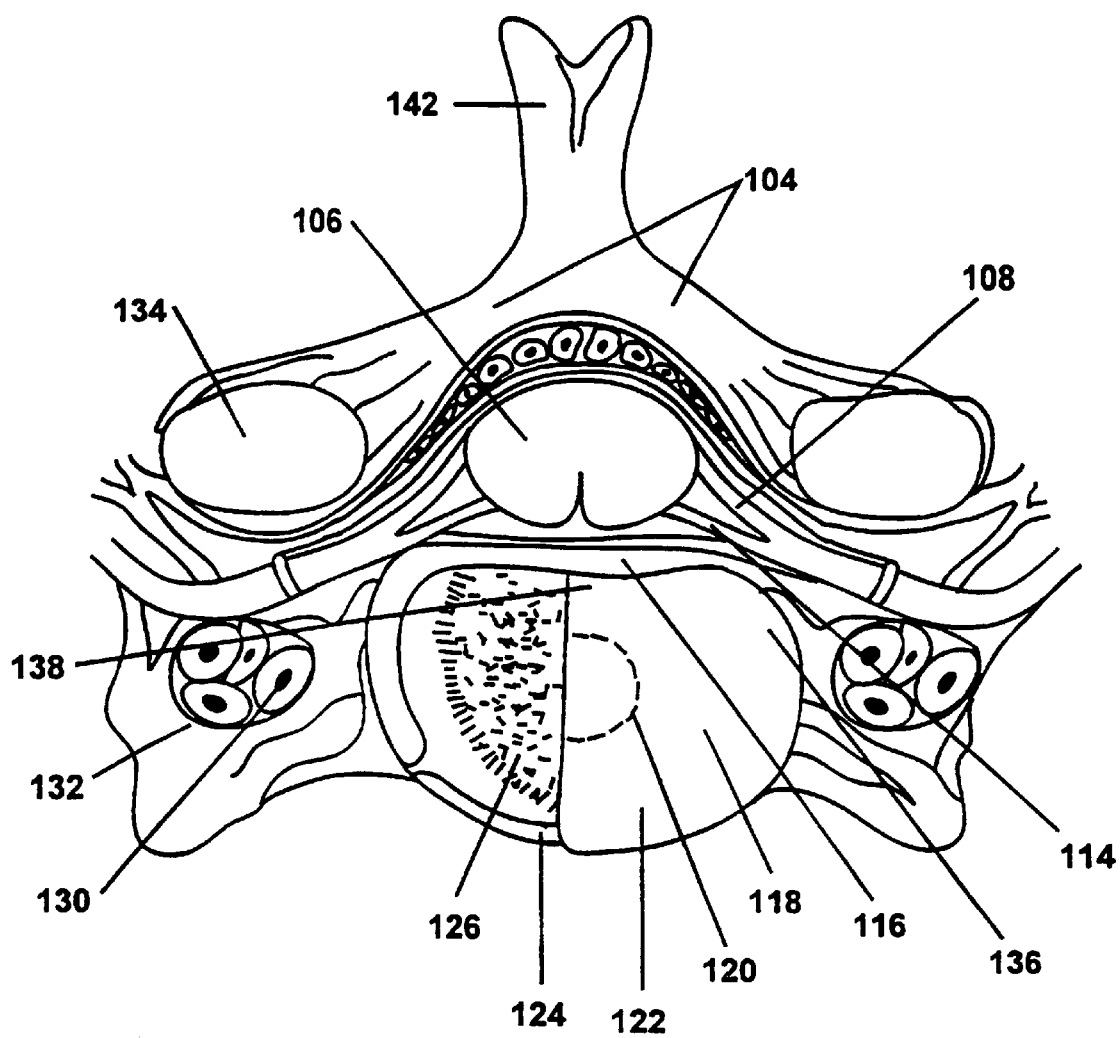
FIG. 1A is a superior cross-sectional anatomical view of a cervical disc and vertebra.
Figure 1B:
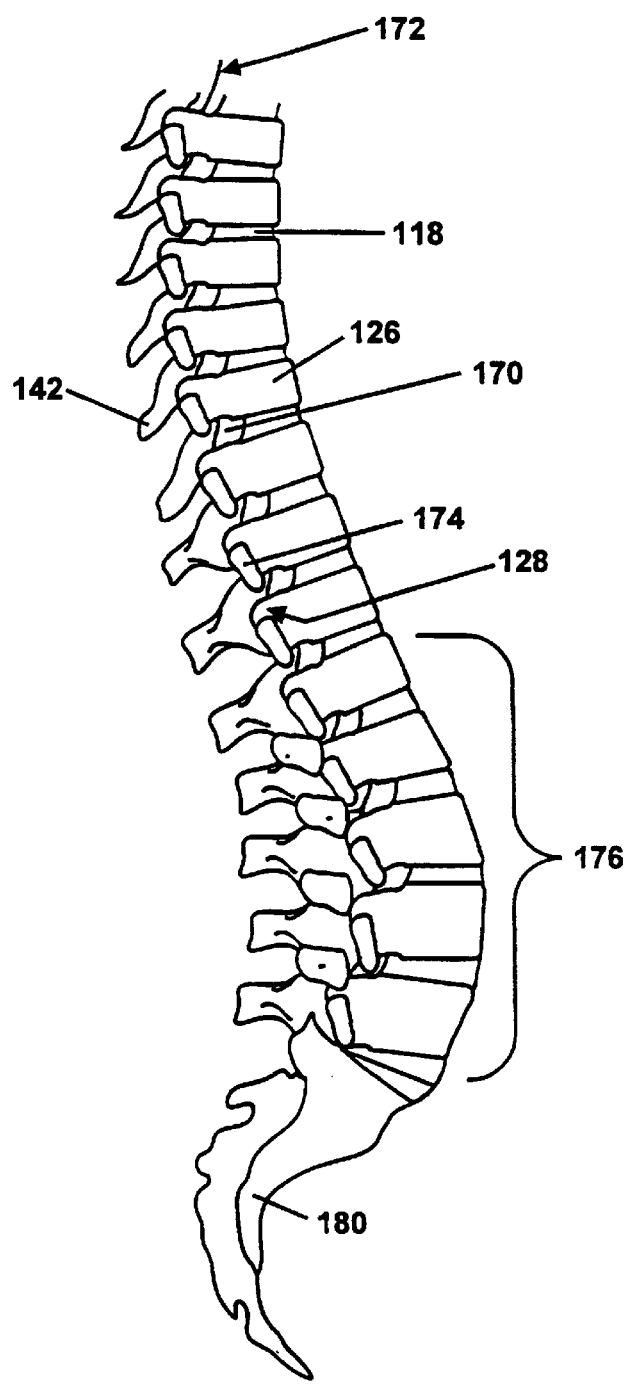
FIG. 1B is a lateral anatomical view of a portion of a lumbar spine.
Figure 1D:
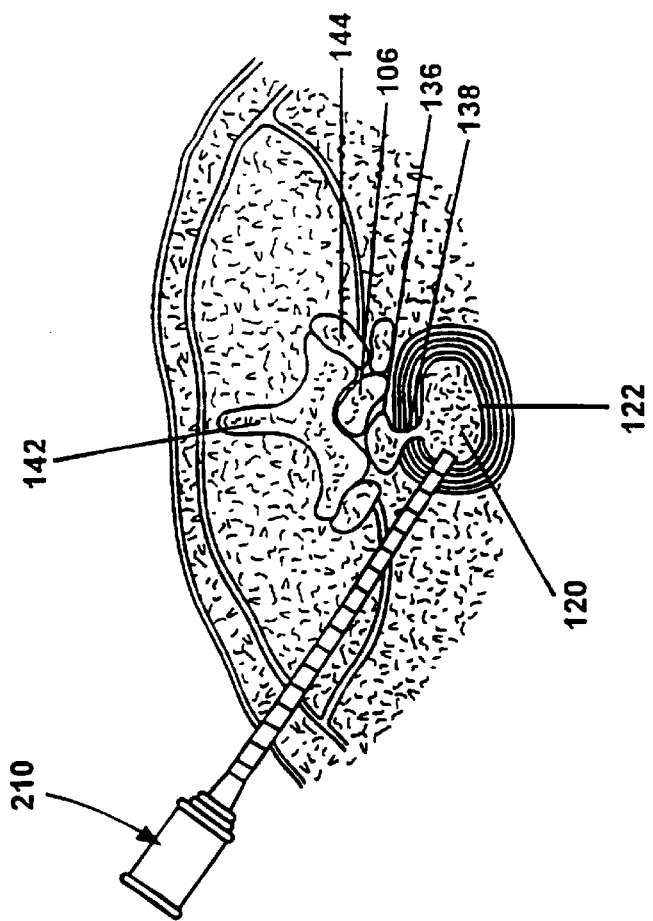
FIG. 1D is a superior cross-sectional view of the required posterior
Figure 1C:
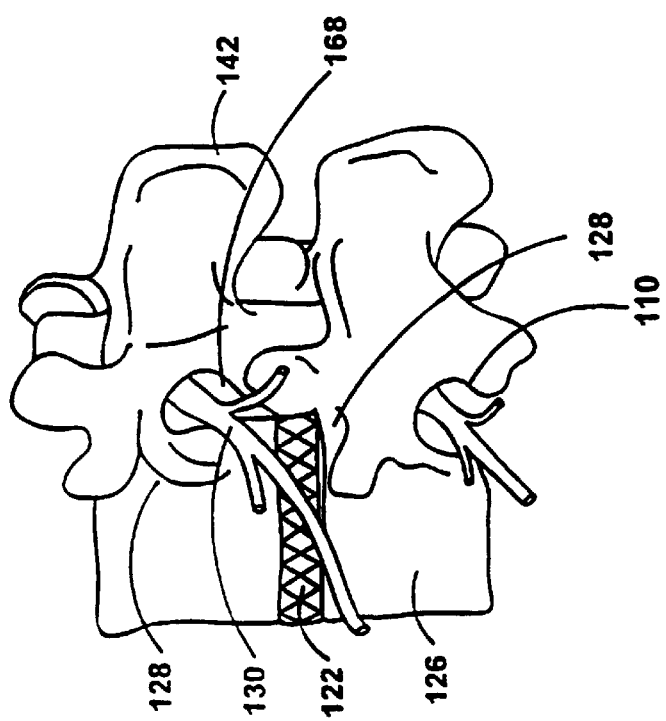
FIG. 1C is a posterior-lateral anatomical view of two lumbar vertebrae and an illustration of the triangular working zone, representing an embodiment of the present invention.

Accordingly, it is desirable to diagnose and treat disc abnormalities such as disc degeneration at locations previously not accessible via percutaneous approaches and without major surgical intervention or substantial destruction to the disc. It would be further desirable to treat disc abnormalities via controlled high-energy input available through radio frequency energy. It would be further desirable to provide such RF energy to the nucleus pulposus at the posterior, posterior lateral and the posterior medial regions of the inner wall of the annulus fibrosis, without heating other regions of the nucleus, as would occur with prior art heating elements. It would further be desirable to be able to administer materials to, or remove materials from, a precise, selected location within the disc, particularly to the location of the annular fissure. It would be further desirable to provide thermal energy into collagen in the area of the fissure to strengthen the annulus and possibly fuse collagen to the sides of the fissure, particularly at the posterior, posterior lateral and the posterior medial regions of the inner wall of the annulus fibrosus.

A primary object of the invention is to provide a minimally invasive method and apparatus for diagnosing and treating fissures of discs at selected locations within the disc.

Another object of the invention is to provide a minimally invasive method and apparatus for treating morphological abnormalities of discs at selected locations within the disc via radio frequency electrodes.

Another object of the invention is to provide a device which has a distal end that is inserted into the disc and accesses the posterior, posterior lateral and the posterior medial regions of the inner wall of the annulus fibrosis for application of RF energy at such location.

Another object of the invention is to provide an apparatus which is advanceable and navigable at the inner wall of the annulus fibrosus to provide localized heating at the site of the annular fissure.

Another object of the invention include providing apparatus and methods for diagnosing an abnormality and/or adding or removing a material at a preselected location of a disc via a functional element.

Another object of the invention is to provide a device which has a distal end that is inserted into the disc and accesses the posterior, posterior lateral and the posterior medial regions of the inner wall of the annulus fibrosis in order to repair or shrink an annular fissure at such a location.

Another object of the invention is to provide a non-destructive method and apparatus for treating morphologic abnormalities of discs.

Another object of the invention is to provide a method and apparatus to treat degenerative intervertebral discs by delivering thermal energy to denervate selective nerves embedded in the walls of the disc.

Another objective of the invention is to provide a method and apparatus to treat degenerative intervertebral discs by delivering thermal energy to cauterize granulation tissue that is ingrown in the wall of the disc.

Another object of the invention is to provide a method and apparatus to treat degenerative intervertebral discs by delivering thermal energy to break down selected enzyme systems and neurotransmitters that generate pain within the disc.

Another object of the invention is to provide a method and apparatus to treat degenerative intervertebral discs by shrinking a selected amount of collagen in the annulus fibrosis of the disc and remove a redundancy in the disc roll.

Another object of the invention is to provide a method and apparatus to treat degenerative intervertebral discs by delivering thermal energy to at least a portion of the nucleus pulposus to reduce water content of the nucleus pulposus and shrink the nucleus pulposus without creating a contained herniated disc.

Another object of the invention is to provide a method and apparatus to treat degenerative intervertebral discs by supplying sufficient thermal energy to shrink the nucleus pulposus and tighten the disc.

Another object of the invention is to provide an apparatus to treat degenerative intervertebral discs which is advanceable and navigational adjacent to an inner wall of the annulus fibrosis.

Another object of the invention is to provide a thermal energy delivery device which has a distal end that is inserted into the nucleus pulposus and accesses the posterior, posterior lateral and the posterior central regions of the inner wall of the nucleus fibrosis.

The invention provides an intervertebral disc apparatus that includes an introducer with an introducer lumen and a catheter. The catheter is at least partially positioned in the introducer lumen and includes an probe section and an energy delivery device coupled to the intradiscal section. The intradiscal section is configured to be advanceable through a nucleus pulposus of the intervertebral disc and positionable adjacent to a selected site of an inner wall of an annulus fibrosis. The energy delivery device is configured to deliver sufficient energy to heat at least a portion of the intervertebral disc without substantially removing intervertebral disc material positioned adjacent to the energy delivery device.

The invention also includes providing an externally guidable intervertebral disc apparatus for manipulation of disc tissue present at a preselected location of an intervertebral disc, the disc having a nucleus pulposus, an annulus fibrosis, and an inner wall of the annulus fibrosis, the nucleus pulposus having a first diameter and a disc playing between opposing sections of the inner wall, proximity to the nucleus being provided by an introducer comprising an internal introducer lumen with an opening at a terminus of the introducer, comprising a catheter having a distal end and a proximal end having a longitudinal access, the catheter being adapted to slidably advance through the introducer lumen, the catheter having an intradiscal section at the distal end of the catheter, the intradiscal section being extendable through the opening of the introducer and having sufficient rigidity to be advanceable through the nucleus pulposus of the disc and around the inner wall of the annulus fibrosis under a force applied longitudinally to the proximal end and having insufficient penetration ability to be advanceable through the inner wall of the annulus fibrosis under the force; and a heating element located at the intradiscal section selected from the group consisting of RF heating elements, resistive heating elements, chemical heating elements, and ultrasound heating elements.

In an embodiment of the invention is based on a catheter for delivering energy to a surgical site. The catheter includes at a proximal end a handle and at a distal end a probe. The catheter includes at least one energy delivery device and an activation element. The at least one energy delivery device is located at the distal end of the catheter to deliver energy to portions of the surgical site. The activation element is located at the distal end of the catheter, to transition the probe from a linear to a multidimensional shape, within the surgical site. In another embodiment of the invention the catheter includes a substrate and a heating element. The substrate is located at the distal end of the catheter. The heating element is fabricated on the substrate by photo-etching to deliver thermal energy to portions of the surgical site.

In another embodiment of the invention the catheter includes a first probe section, at least one energy delivery element, a tip and a blade. The first probe section defines along a length thereof a first lumen. The at least one energy delivery element is located at the distal end of the catheter to deliver energy to portions of the intervertebral disc. The tip is coupled to the first probe section at a terminus thereof. The tip defines on an exterior face a second lumen substantially concentric with said first lumen. The blade is positioned within the first lumen and is extensible from a first position within said first probe section, to a second position extending through the second lumen and beyond the tip, to cut selected portions within the intervertebral disc.

In another embodiment of the invention a catheter includes an energy delivery element, a material transfer element, and at least one interface on the handle thereof. The energy delivery element is located at the distal end of the catheter to deliver energy to portions of the intervertebral disc. The material transfer element is located at the distal end of the catheter to transfer material to and from the intervertebral disc. The at least one interface on the handle couples the energy delivery element and the material transfer element to external devices for energy and material transfer to and from the intervertebral disc.

In still another embodiment of the invention a method for deploying a probe portion of a catheter in a multi-dimensional shape within a surgical site is disclosed. The method includes the steps of: configuring the probe of the catheter in a substantially linear configuration; applying a sufficient force to advance the probe of the catheter through the nucleus pulposus, which force is insufficient to puncture the annulus fibrosus; deploying the probe in a substantially arcuate configuration within the inner wall of the annulus fibrosus, and delivering energy from the probe to portions of the intervertebral disc.

In another embodiment of the invention a catheter for treating an intervertebral disc is disclosed. The catheter includes an electrophoretic element located at the distal end of the catheter to alter the milieu within the intervertebral disc.

DETAILED DESCRIPTION

The present invention provides a method and apparatus for treating intervertebral disc disorders by the application of controlled heating to a localized region of an intervertebral disc. Such disorders include but are not limited to (i) degenerative discs which have tears or fissures in the annulus fibrosis, particularly fissures of the annulus fibrosis, which may or may not be accompanied with contained or escaped extrusions, (ii) contained disc herniations with focal protrusions, and (iii) bulging discs. Such disorders include but are not limited to (i) degenerative discs which have tears or fissures in the annulus fibrosis, (ii) contained disc herniations with focal protrusions, and (iii) bulging discs.

Degenerative discs with tears or fissures are treated non-destructively without the removal of disc tissue other than limited ablation to the nucleus pulposus which changes some of the water content of the nucleus pulposus. Nothing is added to supplement the mechanics of the disc. Electromagnetic energy is delivered to a selected section of the disc in an amount which does not create a destructive lesion to the disc, other than at most a change in the water content of the nucleus pulposus. In one embodiment, there is no removal and/or vaporization of disc material positioned adjacent to an energy delivery device positioned in a nucleus pulposus. Sufficient electromechanical energy is delivered to the disc to change its biochemical, neurophysiologic and/or biomechanical properties. Neurophysiologic modifications include denervation of nociceptors in a tear or fissure in the annulus fibrosis.

Degenerative intervertebral discs with fissures are treated by denervating selected nerves that are embedded in the interior wall of the annulus fibrosis as well as nerves outside of the interior wall including those on the surface of the wall. Electromagnetic energy is used to cauterize granulation tissue which are pain sensitive areas and formed in the annulus fibrosis wall. Electromagnetic energy is also used to break down selected enzyme systems and neurotransmitters that generate pain within the disc. Generally, these enzymes and neurotransmitters only work within a small bandwidth of both pH and temperature.

Electromagnetic energy is applied to shrink collagen in the annulus fibrosis and/or nucleus pulposus. This reduces the redundancy in the disc roll that is created in a degenerative disc. Delivery of electromagnetic energy to the nucleus pulposus removes some water and permits the nucleus pulposus to withdraw. This reduces a "pushing out" effect that created a contained herniation. Combinations of shrinking the disc, shrinking of the nucleus pulposus by reducing water content, as well as tightening up the annulus fibrosis wall creates a rejuvenation of the disc. Reducing the pressure in the disc and tightening the annulus fibrosis produces a favorable biomechanical effect. Application of electromagnetic energy locally increases the stiffness of the disc.

The annulus fibrosis is comprised primarily of fibrosis-like material and the nucleus pulposus is comprised primarily of an amorphous colloidal gel. The distinction between the annulus fibrosis and the nucleus pulposus becomes more difficult to distinguish when a patient is 30 years old or greater. There is often a transition zone between the annulus fibrosis and the nucleus pulposus made of fibrosis-like material and amorphous colloidal gel. For purposes of this disclosure, the inner wall of the annulus fibrosis includes the young wall comprised primarily of fibrosis-like material as well as the transition zone which includes both fibrous-like material and amorphous colloidal gels (hereinafter collectively referred to as "inner wall of the annulus fibrosis").

In general, an apparatus of the invention is in the form of an externally guidable intervertebral disc apparatus for accessing and manipulating disc tissue present at a selected location of an intervertebral disc having a nucleus pulposus and an annulus fibrosus, the annulus having an inner wall. Use of a temperature-controlled energy delivery element, combined with the navigational control of the inventive catheter, provides preferential, localized heating to treat the fissure. For ease of reference to various manipulations and distances described below, the nucleus pulposus can be considered as having a given diameter in a disc plane between opposing sections of the inner wall. This nucleus pulposus diameter measurement allows instrument sizes (and parts of instruments) designed for one size disc to be readily converted to sizes suitable for an instrument designed for a different size of disc.

The operational portion of the apparatus of the invention is brought to a location in or near the disc's fissure using techniques and apparatuses typical of percutaneous interventions. For convenience and to indicate that the apparatus of the invention can be used with any insertional apparatus that provides proximity to the disc, including many such insertional apparatuses known in the art, the term "introducer" is used to describe this aid to the method. An introducer has an internal introducer lumen with a distal opening at a terminus of the introducer to allow insertion (and manipulation) of the operational parts of the apparatus into (and in) the interior of a disc.

The operational part of the apparatus comprises an elongated element referred to as a catheter, various parts of which are located by reference to a distal end and a proximal end at opposite ends of its longitudinal axis. The proximal end is the end closest to the external environment surrounding the body being operated upon (which may still be inside the body in some embodiments if the catheter is attached to a handle insertable into the introducer). The distal end of the catheter is intended to be located inside the disc under conditions of use. The catheter is not necessarily a traditional medical catheter (i.e., an elongate hollow tube for admission or removal of fluids from an internal body cavity) but is a defined term for the purposes of this specification. "Catheter" has been selected as the operant word to describe this part of the apparatus, as the inventive apparatus is a long, flexible tube which transmits energy and/or material from a location external to the body to a location internal to the disc being accessed upon, such as a collagen solution and heat to the annular fissure. Alternatively, material can be transported in the other direction to remove material from the disc, such as removing material by aspiration to decrease pressure which is keeping the fissure open and aggravating the symptoms due to the fissure.

The catheter is adapted to slidably advance through the introducer lumen, the catheter having an probe section at the distal end of the catheter, the probe section being extendible through the distal opening at the terminus of the introducer into the disc. Although the length of the probe portion can vary with the intended function as explained in detail below, a typical distance of extension is at least one-half the diameter of the nucleus pulposus, preferably in the range of one-half to one and one-half times the circumference of the nucleus.

In order that the functional elements of the catheter (e.g., an electromagnetic probe, such as, an RF electrode or a resistance heater) can be readily guided to the desired location within a disc, the probe portion of the catheter is manufactured with sufficient rigidity to avoid collapsing upon itself while being advanced through the nucleus pulposus and navigated around the inner wall of the annulus fibrosus. The probe portion, however, has insufficient rigidity to puncture the annulus fibrosus under the same force used to advance the catheter through the nucleus pulposus and around the inner wall of the annulus fibrosus. Absolute penetration ability will vary with sharpness and stiffness of the tip of the catheter, but in all cases a catheter of the present invention will advance more readily through the nucleus pulposus than through the annulus fibrosus.

In preferred embodiments, the probe section of the catheter further has differential bending ability in two orthogonal directions at right angles to the longitudinal axis. This causes the catheter to bend along a desired plane (instead of at random). Also when a torsional (twisting) force is applied to the proximal end of the catheter to re-orient the distal end of the catheter, controlled advancement of the catheter in the desired plane is possible.

A further component of the catheter is a functional element located in the probe section for diagnosis or for adding energy and adding and/or removing material at the selected location of the disc where the annular tear is to be treated. The apparatus allows the functional element to be controllably guided by manipulation of the proximal end of the catheter into a selected location for localized treatment of the annular fissure.

The method of the invention, which involves manipulating disc tissue at the annular fissure, is easily carried out with an apparatus of the invention. An introducer is provided that is located in a patient's body so that its proximal end is external to the body and the distal opening of its lumen is internal to the body and (1) internal to the annulus fibrosus or (2) adjacent to an annular opening leading to the nucleus pulposus, such as an annular tear or trocar puncture that communicates with the nucleus pulposus. The catheter is then slid into position in and through the introducer lumen so that the functional element in the catheter is positioned at the selected location of the disc by advancing or retracting the catheter in the introducer lumen and optionally twisting the proximal end of the catheter to precisely navigate the catheter. By careful selection of the rigidity of the catheter and by making it sufficiently blunt to not penetrate the annulus fibrosus, and by careful selection of the flexibility in one plane versus the orthogonal plane, the distal portion of the catheter will curve along the inner wall of the annulus fibrosus as it is navigated and is selectively guided to an annular tear at selected location(s) in the disc. Energy is applied and/or material is added or removed at the selected location of the disc via the functional element.

Each of the elements of the apparatus and method will now be described in more detail. However, a brief description of disc anatomy is provided first, as sizes and orientation of structural elements of the apparatus and operations of the method can be better understood in some cases by reference to disc anatomy.

An Exemplary Surgical Site

The annulus fibrosus is comprised primarily of tough fibrous material, while the nucleus pulposus is comprised primarily of an amorphous colloidal gel. There is a transition zone between the annulus fibrosus and the nucleus pulposus made of both fibrous-like material and amorphous colloidal gel. The border between the annulus fibrosus and the nucleus pulposus becomes more difficult to distinguish as a patient ages, due to degenerative changes. This process may begin as early as 30 years of age. For purposes of this specification, the inner wall of the annulus fibrosus can include the young wall comprised primarily of fibrous material as well as the transition zone which includes both fibrous material and amorphous colloidal gels (hereafter collectively referred to as the "inner wall of the annulus fibrosus"). Functionally, that location at which there is an increase in resistance to catheter penetration and which is sufficient to cause bending of the distal portion of the catheter into a radius less than that of the internal wall of the annulus fibrosus is considered to be the "inner wall of the annulus fibrosus."

As with any medical instrument and method, not all patients can be treated, especially when their disease or injury is too severe. There is a medical gradation of degenerative disc disease (stages 1–5). See, for example, Adams et al., "The Stages of Disc Degeneration as Revealed by Discograms," J. Bone and Joint Surgery, 68, 36–41 (1986). As these grades are commonly understood, the methods of instrument navigation described herein would probably not be able to distinguish between the nucleus and the annulus in degenerative disease of grade 5. In any case, most treatment is expected to be performed in discs in stages 3 and 4, as stages 1 and 2 are asymptomatic in most patients, and stage 5 may require disc removal and fusion.

Some of the following discussion refers to motion of the catheter inside the disc by use of the terms "disc plane," "oblique plane" and "cephalo-caudal plane." These specific terms refer to orientations of the catheter within the intervertebral disc.

Referring now to the figures, FIGS. 2A and 2B illustrate one embodiment of a catheter 200 of the invention as it would appear inserted into the lumen 214 of an introducer 210. The apparatus shown is not to scale, as an exemplary apparatus (as will be clear from the device dimensions below) would be relatively longer and thinner; the proportions used in FIG. 2A were selected for easier viewing by the reader. The catheter 200 includes handle 206, stem 208, probe section 216 and a tip 220. The handle 206 at the proximal end of the catheter is coupled via the stem 208 to the probe section 216, which is located proximate the distal end of the device. At the terminus of the probe, i.e., the distal end of the device, is the tip 220. The tip may be axially displaced from the probe section. Functional elements 222 for delivery or energy or material to or from the site may be placed within the probe. These may, via connections within the probe, stem and handle, be coupled to either an energy delivery device 202 or a material transfer device 204. Therefore no limitation should be placed on the types of energy, force, or material transporting elements present in the catheter. These are merely some of the possible alternative functional elements that can be included in the probe portion of the catheter. The flexible, movable catheter 200 is at least partially positionable in the introducer lumen 214, to bring the probe section, which is designed to be the portion of the catheter that will be pushed out of the introducer lumen and into the nucleus pulposus and into the selected location(s) with regard to the annular tear. Dashed lines are used to illustrate bending of the probe portion of the catheter as it might appear under use, as discussed in detail later in the specification.

FIG. 2B shows an axial cross-section of stem 208 at the proximal end of the catheter. In this embodiment of the invention the stem has an oval shape, as does the lumen 214 thus allowing the rotational orientation of the probe to be fixed with respect to the introducer. Other sections and properties of catheter 200 are described later.

For one embodiment suitable for intervertebral discs, the outer diameter of catheter 200 is in the range of 0.2 to 5 mm, the total length of catheter 200 (including the portion inside the introducer) is in the range of 10 to 60 cm, and the length of introducer 210 is in the range of 5 to 50 cm. For one preferred embodiment, the catheter has a diameter of 1 mm, an overall length of 30 cm, and an introduced length of 15 cm (for the probe section). With an instrument of this size, a physician can insert the catheter for a distance sufficient to reach selected location(s) in the nucleus of a human intervertebral disc.

Any device in which bending of the tip of a catheter of the invention is at least partially controlled by the physician is "actively steerable." A mandrel may facilitate the active steering of a catheter.

Active Steering of Catheter

Referring now to FIG. 2B, a guiding mandrel 232 can be included both to add rigidity to the catheter and to inhibit movement of probe section 216 of the catheter 200 along an inferior axis 242 while allowing it along a superior axis 240 while positioned and aligned in the disc plane of a nucleus pulposus 120. This aids the functions of preventing undesired contact with a vertebra and facilitating navigation. The mandrel can be flattened to encourage bending in a plane (the "plane of the bend") orthogonal to the "flat" side of the mandrel. "Flat" here is a relative term, as the mandrel can have a D-shaped cross-section, or even an oval or other cross-sectional shape without a planar face on any part of the structure. Regardless of the exact configuration, bending will preferentially occur in the plane formed by the principal longitudinal axis of the mandrel and a line connecting the opposite sides of the shortest cross-sectional dimension of the mandrel (the "thin" dimension). To provide sufficient resistance to the catheter bending out of the desired plane while encouraging bending in the desired plane, the minimum ratio is 1.25:1 ("thickest" to "thinnest" cross-sectional dimensions along at least a portion of the probe section). The maximum ratio is 20:1, with the preferred ratio being between 1.5:1 and 16:3, more preferably between 2:1 and 3.5:1. These ratios are for a solid mandrel and apply to any material, as deflection under stress for uniform solids is inversely proportional to the thickness of the solid in the direction (dimension) in which bending is taking place. For other types of mandrels (e.g., hollow or non-uniform materials), selection of dimensions and/or materials that provide the same relative bending motions under stress are preferred.

A catheter of the present invention is designed with sufficient torsional strength (resistance to twisting) to prevent undesired directional movement of the catheter. Mandrels formed from materials having tensile strengths in the range set forth in the examples of this specification provide a portion of the desired torsional strength. Other materials can be substituted so long as they provide the operational functions described in the examples and desired operating parameters.

While the mandrel can provide a significant portion of the column strength, selective flexibility, and torsional strength of a catheter, other structural elements of the catheter also contribute to these characteristics. Accordingly, it must be kept in mind that it is the characteristics of the overall catheter that determine suitability of a particular catheter for use in the methods of the invention. Similarly, components inside the catheter, such as a heating element or potting compound, can be used to strengthen the catheter or provide directional flexibility at the locations of these elements along the catheter.

It is not necessary that the guiding mandrel 232 be flattened along its entire length. Different mandrels can be designed for different sized discs, both because of variations in disc sizes from individual to individual and because of variations in size from disc to disc in one patient. The bendable portion of the mandrel is preferably sufficient to allow probe section 216 of the catheter to navigate at least partially around the circumference of the inner wall of the annulus fibrosus (so that the operational functions of the catheter can be carried out at desired location(s) along the inner wall of the annulus fibrosus). Shorter bendable sections are acceptable for specialized instruments. In most cases, a flattened distal portion of the mandrel of at least 10 mm, preferably 25 mm, is satisfactory. The flattened portion can extend as much as the entire length of the mandrel, with some embodiments being flattened for less than 15 cm, in other cases for less than 10 cm, of the distal end of the guide mandrel.

In preferred embodiments, the guide mandrel or other differential bending control element is maintained in a readily determinable orientation by a control element located at the proximal end of the catheter. The orientation of the direction of bending and its amount can be readily observed and controlled by the physician. One possible control element is simply a portion of the mandrel that extends out of the proximal end of the introducer and can be grasped by the physician, with a shape being provided that enables the physician to determine the orientation of the distal portion by orientation of the portion in the hand. For example, a flattened shape can be provided that mimics the shape at the distal end (optionally made larger to allow better control in the gloved hand of the physician, as in the handle 206 of FIG. 2A). More complex proximal control elements capable of grasping the proximal end of the mandrel or other bending control element can be used if desired, including but not limited to electronic, mechanical, and hydraulic controls for actuation by the physician.

The guide mandrel can also provide the function of differential flexibility by varying the thickness in one or more dimensions (for example, the "thin" dimension, the "thick" dimension, or both) along the length of the mandrel. A guide mandrel that tapers (becomes gradually thinner) toward the distal tip of the mandrel will be more flexible and easier to bend at the tip than it is at other locations along the mandrel. A guide mandrel that has a thicker or more rounded tip than more proximal portions of the mandrel will resist bending at the tip but aid bending at more proximal locations. Thickening (or thinning) can also occur in other locations along the mandrel. Control of the direction of bending can be accomplished by making the mandrel more round, i.e., closer to having 1:1 diameter ratios; flatter in different sections of the mandrel; or by varying the absolute dimensions (increasing or decreasing the diameter). Such control over flexibility allows instruments to be designed that minimize bending in some desired locations (such as the location of connector of an electrical element to avoid disruption of the connection) while encouraging bending in other locations (e.g., between sensitive functional elements). In this manner, a catheter that is uniformly flexible along its entire length, is variably flexibility along its entire length, or has alternating more flexible and less flexible segment(s), is readily obtained simply by manufacturing the guide mandrel with appropriate thickness at different distances and in different orientations along the length of the mandrel. Such a catheter will have two or more different radii of curvature in different segments of the catheter under the same bending force.

In some preferred embodiments, the most distal 3 to 40 mm of a guide mandrel is thinner relative to central portions of the probe section to provide greater flexibility, with the proximal 10 to 40 mm of the probe section being thicker and less flexible to add column strength and facilitate navigation.

The actual dimensions of the guide mandrel will vary with the stiffness and tensile strength of the material used to form the mandrel. In most cases the mandrel will be formed from a metal (elemental or an alloy) or plastic that will be selected so that the resulting catheter will have characteristics of stiffness and bending that fall within the stated limits. Additional examples of ways to vary the stiffness and tensile strength include transverse breaks in a material, advance of the material so that it "doubles up," additional layers of the same or different material, tensioning or relaxing tension on the catheter, and applying electricity to a memory metal.

Multi-Dimensional Probe Deployment

Catheters which are actively steerable, may include additionally the capability of deploying into planar substantially two dimensional shapes or three dimensional shapes which conform to the surgical site. These multi-dimensional deployment capabilities, reduce operating time, improve operational accuracy and increase the utility of surgical intervention.

Linear to Arcuate Transition of Probe

The following FIGS. 3–9 show apparatus and methods for transitioning a probe from a linear to a multi-dimensional shape. The transition of the probe from a linear to an arcuate shape may be brought about by any of a group of activation elements including, but not limited to, the following.

In an embodiment of the invention the probe may include a resilient material, e.g. a heat treated metal or spring metal, which will assume a linear shape only by virtue of the guiding force of the lumen portion of the introducer and will resume its original arcuate shape, upon introduction to the surgical site and by extension beyond the confines of the introducer. The resilient spring-like material is arcuate in the absence of external stress but, under selected stress conditions (for example, while the catheter is inside the introducer), is linear. Such a biased distal portion can be manufactured from either spring metal or superelastic memory material (such as Tinel® nickel-titanium alloy, Raychem Corp., Menlo Park, Calif.). The introducer (at least in the case of a spring-like material for forming the catheter) is sufficiently strong to resist the bending action of the bent tip and maintain the biased distal portion in alignment as it passes through the introducer. Compared to unbiased catheters, a catheter with a biased probe encourages advancement of the probe substantially in the direction of the bend relative to other lateral directions. Biasing the catheter tip also further decreases likelihood that the tip will be forced through the annulus fibrosus under the pressure used to advance the catheter. In those embodiments utilizing a resilient material an introducer in combination with the resilient material is necessary in order to introduce the probe in a linear or lay flat configuration to the surgical site.

Although an introducer may also be used with any of the following activation elements it is not necessary to bring about the transition from a linear to an arcuate shape.

In another embodiment of the invention the probe may at least two materials with a different coefficient of thermal expansion joined to one another along their length, such that at one temperature, e.g. room temperature they are linear while at an elevated temperature, the differential expansion of one with respect to the other induces an arcuate bending of both. Bi-metallic strips such as copper and steel might serve this function. Any other two metals with different coefficients of expansion could be substituted for copper and steel. The greater the differential of the coefficients of expansion between the two metals the smaller the radius(s) of the arcuate shape formed thereby at any given temperature differential. Other materials besides metals with different coefficients of expansion could also be used. The temperature differential of the at least two materials at room temperature and at the surgical site may be increased by energy delivered to the probe, e. g. RF or resistive heating. Alternately, electrical power may be directly applied directly to one or both of the at least two materials provided they are electrically resistive such that the application of power will result in heat generation.

In another embodiment of the invention the arcuate shape may be brought about by use of materials with temperature dependent shape memory such as the metal alloy Nitinol. The probe is fabricated to be linear at room temperature and arcuate at the temperature of the surgical site. The temperature differential of the Nitenol at room temperature and at the surgical site may be increased by energy delivered to the probe, e. g. RF or resistive heating. Alternately the electrical power may be directly applied directly to the Nitenol which is itself a resistive element.

In another embodiment of the invention the arcuate shape may be induced electrical activated expansion and contraction of materials within the probe. Piezo-electric crystals positioned on either the exterior or interior radius of the arc may be used in this manner to respectively expand or contract against a surface of a mandrel within the probe, to induce an arcuate shape.

In still another embodiment of the invention the alteration of shape from linear to arcuate may be produced by mechanical means such as the combination of a draw wire and mandrel, coupled at the tip of the device and extending the length of the catheter, such that tension of the draw wire induces tension on a side of the mandrel inducing it to assume an arcuate shape. Numerous combinations of material and energy, either thermal or electrical can be used to create a deformable tip.

An advantageous feature of all the probes set forth in the current invention is that their shape can be configured to conform to the interior shape of the surgical site to which they are introduced, thus placing functional elements on the probe into proximity with all portions of the surgical site without the need for a point-by-point navigation of the probe tip about the surgical site.

Figure 3:
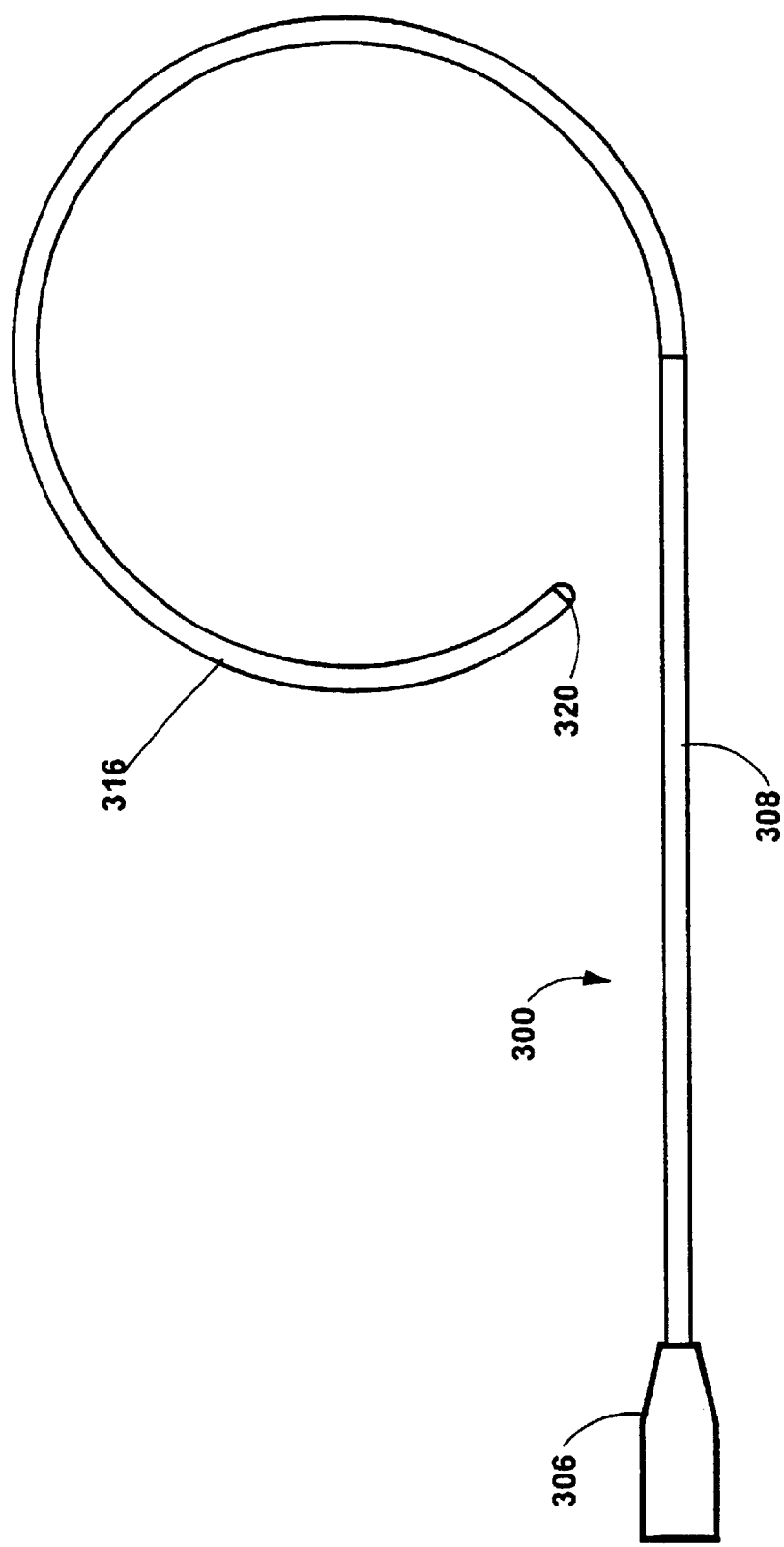
FIG. 3 is a side view of a catheter with a elastically deformed end section with an arcuate shape.

FIG. 3 shows an embodiment of a surgical catheter with a shape shifting probe portion. The catheter 300 includes handle 306, stem 308 probe section 316 and tip 320. The handle 306 at the proximal end of the catheter is coupled via the stem 308 to the probe section 316, which is located proximate the distal end of the device. At the terminus of the probe, i.e., the distal end of the device, is the tip 320. In the embodiment show the probe is fabricated from a resilient material thus requiring an introducer to effect its transition from a linear to an arcuate shape. In alternate embodiments any of the other activation elements described above could be utilized to effect a transition of the probe section from a linear to a multi-dimensional shape.

FIGS. 4A–D show the sequence of operations associated with the insertion of the probe section 316 of the catheter 300 shown in FIG. 3 into the nucleus pulposus 120 of a spinal disc. In FIG. 4A the terminus of lumen 214 (See FIG. 2A) has been introduced into the nucleus pulposus of the disc substantially tangent to the interior sidewall of the disc.

In FIG. 4B handle and stem, respectively, 306–308 of the catheter are inserted further into the introducer 210 so that the tip 320 of the probe section begins to extrude into the intradiscal space.

In FIGS. 4C–D the insertion continues until the probe section 316 has formed a complete circle, with the tip 320 adjacent to the lumen 214 of the introducer 210. In the embodiment shown, the plane defined by the arcuate probe is coplanar with the intradiscal plane defined by the intervertebral disc. Once the probe has deployed within the intradiscal cavity it may be further positioned by movement either of the introducer or the catheter. When the probe is properly deployed, functional elements on the probe may be used to introduce heating or cooling of the intradiscal cavity or of selected portions thereof (See FIGS. 10A–B, 11). In alternate embodiments of the invention the functional element may include a lumen for the introduction and/or removal of material into the surgical site. (See FIGS. 12A–C). In still other embodiments in the invention the probe tip may include a surgical knife, either alone or in combination with a lumen. (See FIGS. 12A–C).

To trace the location of a catheter probe within a surgical site various imaging techniques may be used. A radiographically opaque marking device can be included in the distal portion of the catheter (such as in the tip or at spaced locations throughout the probe portion) so that advancement and positioning of the probe section can be directly observed by radiographic imaging. Such radiographically opaque markings are preferred when the probe section is not clearly visible by radiographic imaging, such as when the majority of the catheter is made of plastic instead of metal. A radiographically opaque marking can be any of the known (or newly discovered) materials or devices with significant opacity. Examples include but are not limited to a steel mandrel sufficiently thick to be visible on fluoroscopy, a tantalum/polyurethane tip, a gold-plated tip, bands of platinum, stainless steel or gold, soldered spots of gold and polymeric materials with radiographically opaque filler such as barium sulfate. A resistive heating element or an RF electrode(s) may provide sufficient radio-opacity in some embodiments to serve as a marking device.

Figure 5:
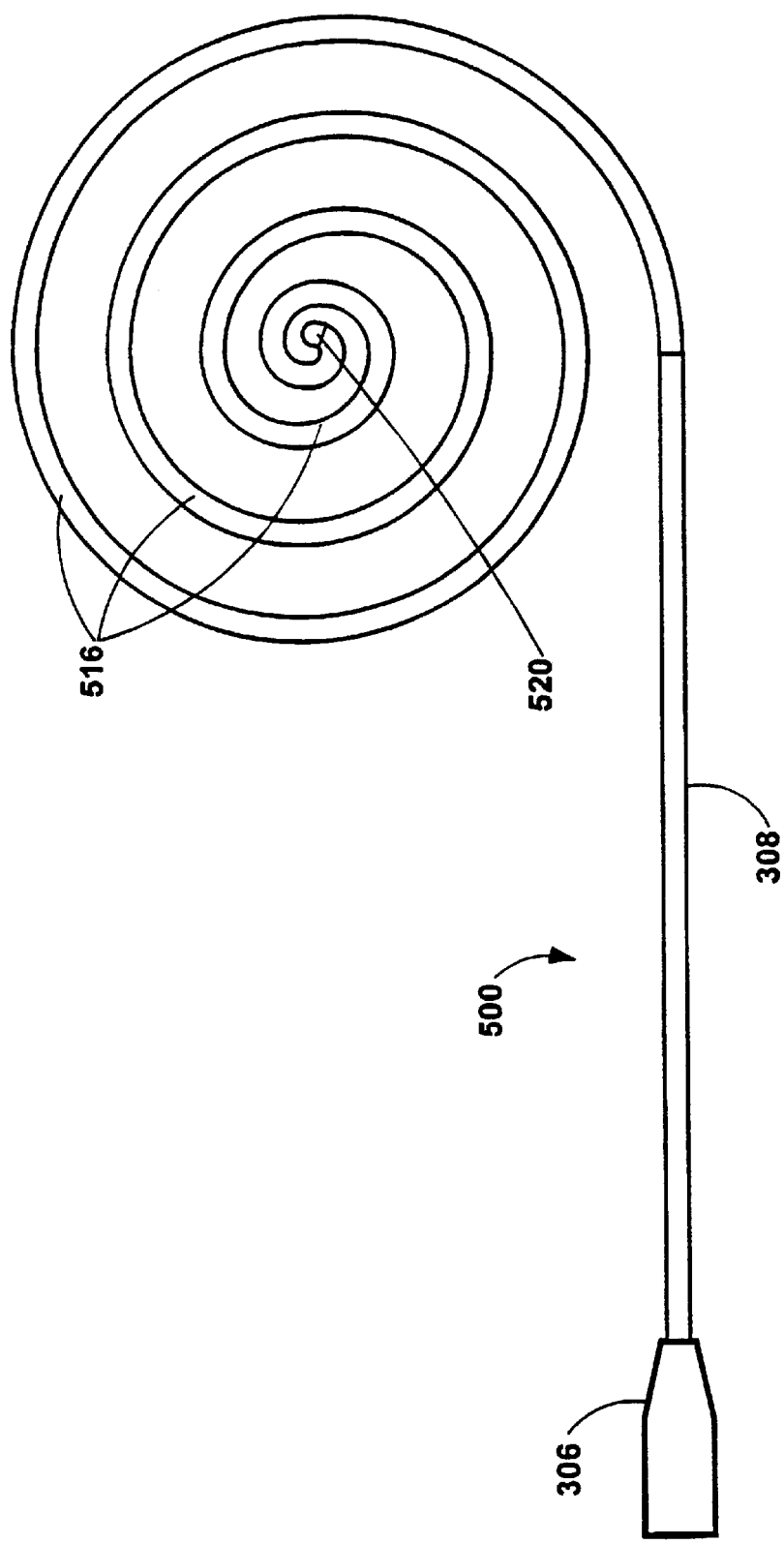
FIG. 5 is a side view of a catheter with a elastically deformed end section with an inward spiral shape.

FIG. 5 shows an alternate embodiment of the catheter with an inward spiraling probe portion. The catheter 500 has a handle 306 coupled via stem 308 to the spiral probe section 516. The spiral probe section terminates at the distal end of the catheter in a tip 520.

As described and discussed above, the catheter may be cause to attain a spiral shape by numerous activation elements including the use of materials which are: resilient or bimetallic, which exhibit temperature dependent shape memory, by materials in which electrical expansion and contraction may be induced, and by mechanical means. A possible advantage of the inward spiraling shape is that material may be swept during deployment of the probe radially inward/outward.

FIGS. 6A–B show respectively elevation and side views of an alternate embodiment of a catheter with a catheter 600 with an outward spiraling probe. Probe section 616 is coupled via stem 308 to handle 306. Tip 620 is at the terminus of the Probe 616 at the distal end of the catheter 600. As is evident in FIG. 6B the stem 308 intersects at an acute angle the plane defined by the spiral probe section 616. Such alteration of the plane of the probe with respect to the stem may result in improved conformity of the probe with the intradiscal cavity or other joint into which the probe may be introduced.

As described and discussed above, the catheter may be cause to attain a spiral shape by numerous activation elements including the use of materials which are: resilient or bimetallic, which exhibit temperature dependent shape memory, by materials in which electrical expansion and contraction may be induced, and by mechanical means. A possible advantage of the outward spiraling shape is that material may be swept during deployment of the probe radially inward/outward.

Figure 7:
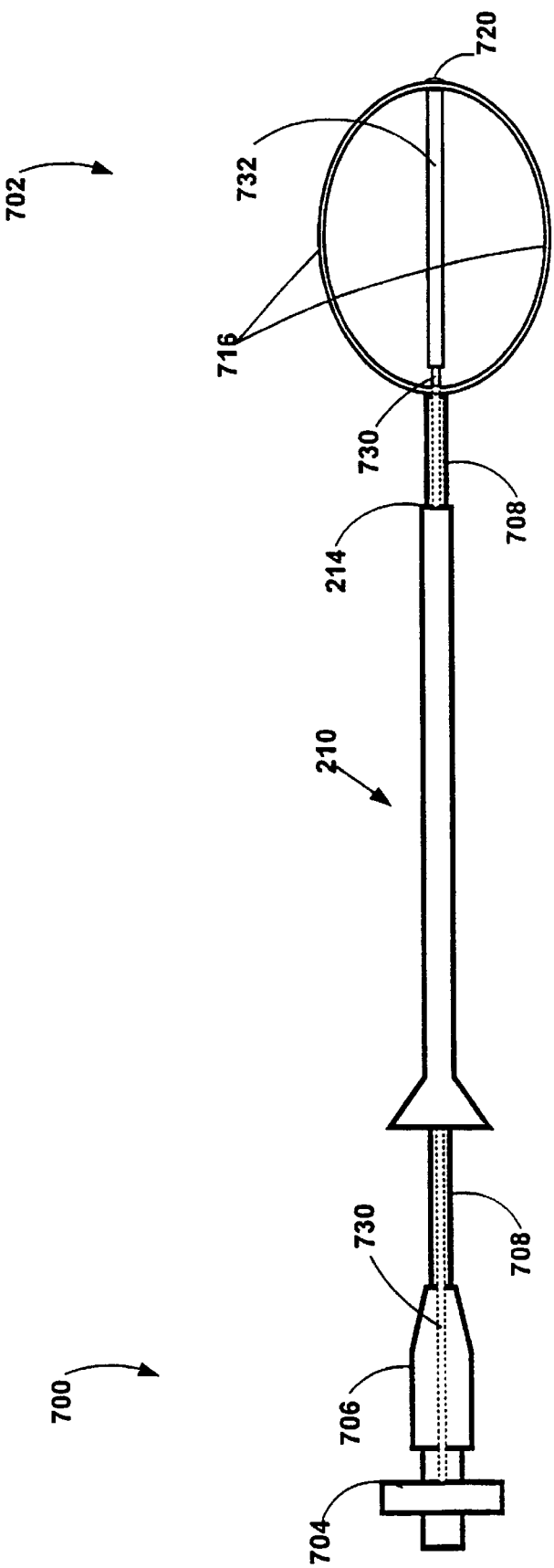
FIG. 7 is a side view of a catheter with a elastically deformed end section with an "eggbeater" shape.

The catheter 700 shown in FIG. 7-8 may be fabricated to deploy into either a planar two dimensional shape or into a three dimensional "eggbeater" shape which conforms to the surgical site. The catheter includes a handle 706, a stem 708, a probe 702 and an introducer 210. The handle 706 includes a push/pull member 704. The stem 708 includes a draw member 730. The introducer 210 includes an internal lumen 214. The probe 702 includes side members 716 and a core member 732.

One or more of the side members 716 are arranged radially about core member 732. The core extends axially and is attached at a distal end of the probe 702 to the distal ends of the side members by tip 720. At a proximal end the core joins with the draw member 730 as an axial extension thereof. The proximal ends of the side members 716 are slidably affixed to the draw member. Axially induced movement of the proximal ends of the side members along that draw member and toward the core member 732 results in an arcuate deflection of the side members from a collapsed position adjacent to the axial core to an expanded position radially displaced about the axial core. The draw member 730 extends axially the full length of the stem 708 and of the handle 706 to a point of attachment at the push/pull member 704 of the handle. The draw member is slidable axially within the stem. The push/pull member 704 of the handle 706 is slidable axially with respect to the handle 706.

In operation the side members 716 are brought into a lay-flat condition against the axial core prior to introduction into the introducer. This situation is brought about by the positioning of push-pull member adjacent to the handle 706. This causes the maximal extension of the draw member from a distal end of the stem 708. In an embodiment of the invention the lay-flat members are tension springs, which in the relaxed position lay flat against the axial core. In this linear configuration, the tip 720 of the probe is placed into the introducer 210. When the probe 702 is extended beyond the introducer and into the surgical site, the draw member is gradually retracted into the handle by a displacement of the push-pull member 704 away from the base portion of the handle 706. This causes the distal end of the stem 708 to press the distal ends of the side members 716, thereby reducing the axial distance between those members and the tip 720. As the distance is reduced, those members assume an arcuate shape radially displaced about the axial core.

In an alternate embodiment of the invention, the side members in a relaxed position assume an arcuate shape radially displaced about the axial core. By coupling the distal end of step 708 to the distal ends of the side member, an extension of the draw member resulting from movement of the push-pull member 704 toward the base portion of the handle 706 causes the side members to lay flat against the axial core.

As described and discussed above, the catheter may be cause to attain the "eggbeater" or other shapes by numerous activation elements including the use of materials which are: resilient or bimetallic, which exhibit temperature dependent shape memory, by materials in which electrical expansion and contraction may be induced, and by mechanical means.

An Electrophoretic Functional Element

The functional element of the probes shown in FIGS. 8A–F perform an electrophoretic function with surgically beneficial results. Electrophoresis can be defined as the movement of charged particles or substances through a medium in which they are dispersed as a result of changes in electrical potential. For example, electrophoretic methods are useful in the separating various molecular particles depending upon the size and shape of the particle, the charge carried, the applied current and the resistance of the medium. In addition, with the appropriate construction of the anode (positive) and the cathode (negative) electrodes, the chemical milieu of a surgical site, e.g. the nucleus pulposus, can be altered by electrophoretic methods, with beneficial therapeutic effects such as pain reduction or intradiscal repair.

In a clinical setting, negatively charged ions or free radicals may be found in high concentrations in chronically inflamed states of surgical sites such as the intradiscal cavity of the spine. Disco-genic pain may for example be associated with higher than normal concentrations of enzymes such as phospholipase A-2 in the spinal disc wall, or the nucleus pulposus for example. Alternately, a recently discovered short protein binds to cell membranes in the brain and spinal cord and may be affected and controlled by electrophoretic methods. The peptide, nocistatin, seemed to block pain or the transmission of pain to the nociceptors or pain receptors when injected into animals. Nocistatin appears to interact with the peptide nociceptin in a manner which may either amplify or reduce pain depending on the relative concentrations of the two peptides. Control of the these two peptides by electrophoresis may prove beneficial in the treatment of back pain.

By inserting a probe into the site with a functional element capable of performing an electrophoretic function, it may be possible to reduce the concentrations of the charged particles: e.g. enzymes, neurotransmitters, proteins, individual molecules, or free radicals to achieve one or more beneficial therapeutic effects including but not limited to pain reduction, intradiscal reshaping or repair.

The concentrations may be reduced by migration of the charged particles from perimeter regions of the surgical site toward the core of the site, by means of an appropriately configured probe, with electrodes positioned at the perimeter and core of the surgical site, which electrodes are charged in a manner designed to encourage whichever of a radially outward or inward migration of the charged particles is therapeutically beneficial.

In an embodiment of the invention, further beneficial effects may be achieved when the charge on the probe is maintained as it is withdrawn from the surgical site, thus encouraging the removal of the charged particles from the site.

FIGS. 8A–F show multi-dimensional probes with side and core members deployed into a multi-dimensional configuration at the surgical site. The side and core members may perform an electrophoretic function by means of electrical stimulus of opposite polarity applied to each. The electrical stimulus may be pure DC or rectified AC at frequencies including the radio frequency range.

Figure 8A:
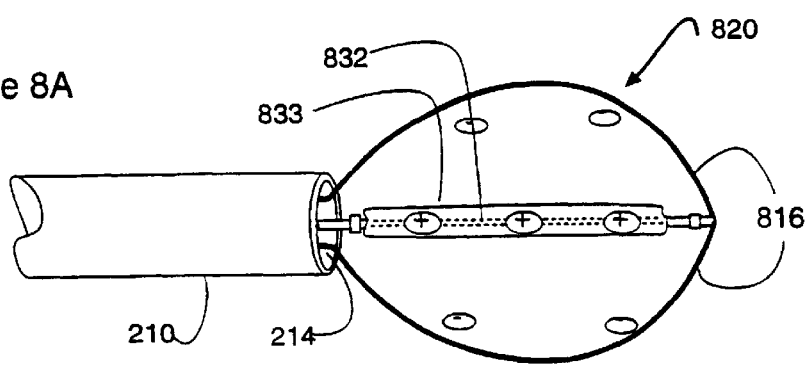
FIGS. 8A–F are isometric views of an alternate embodiment of the invention in which the probe of the catheter performs an electrophoretic function.

In FIG. 8A, side members 816 naturally assume an arcuate configuration radially displaced about core 832. They may be compressed against the core as is the case when they are within the lumen 214 within the introducer 210. As they collectively extended through the lumen and into the surgical site their internal spring tension causes them to assume an arcuate configuration radially displaced about the core. At the completion of the surgery they may be withdrawn into the lumen, and in so doing, collapse against the core.

In an embodiment of the invention central core 832 provides structural support to the tip of the probe. Additionally, central core 832 is surrounded by membrane 833 which serves as a central collector region for the electrophoresis. In another embodiment of the invention the membrane 833 may itself serve as an electrode.

As described and discussed above, the catheter may be caused to attain the "eggbeater" or other shapes by numerous activation elements including the use of materials which are: resilient or bi-metallic, which exhibit temperature dependent shape memory, by materials in which electrical expansion and contraction may be induced, and by mechanical means.

Via electrical connections, the side members 816 and core 832 may perform as electrodes. In an embodiment of the invention the side members and core member are coupled to electrical power to serve as respectively either anodes-cathode or cathodes-anode to one another. The electrical connections couple the electrodes to a source of power which may be located in the catheter or be externally coupled to the electrodes through a coupling on the handle of the catheter. (See FIGS. 13–14). This arrangement may have certain surgical benefits.

By allowing the side members and core to serve as respectively perimeter and core electrodes the core can be charged providing an electrical gradient for electrophoresis to pull charged particles from a perimeter region in the disc to the core. The charge of the core 832 electrode may be continuously maintained during collapse of the side members and retraction of the probe from the surgical site, to remove the charged particles from the surgical site, e.g. the nucleus pulposus. This would effect a change to the nucleus pulposus and reduce the electrical potential on the nociceptors, i.e. pain receptors, thereby reducing pain perception as well as removing material from the disc.

In another embodiment of the invention, electrically charged particles may be introduced into the intradiscal cavity by means of membrane 833. Upon deployment of the side members at the surgical site, and appropriate charging of the side and perimeter members the charged particles may be encouraged to migrate toward the side members thereby affecting a change of the chemical milieu of the site.

Figure 8B:
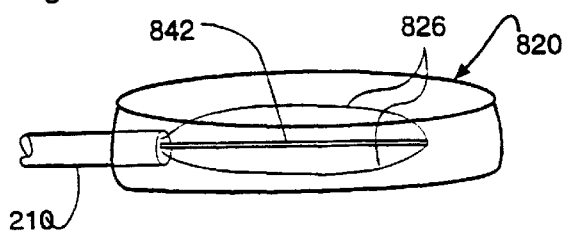
Figure 8C:
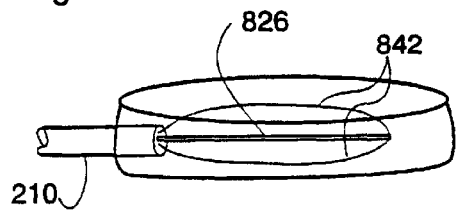
Figure 8D:
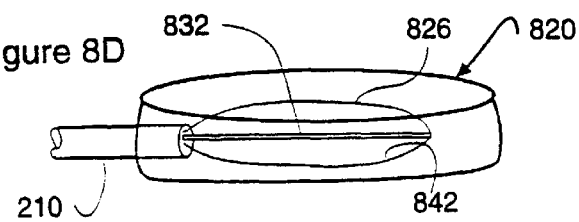

FIGS. 8B–D shows demonstratively alternate functional embodiments of the probe 820 deployed in relation to the intradiscal cavity which contains the nucleus pulposus 120.

FIG. 8B shows one functional embodiment of the invention where side structural members serve as a cathode 826 while central core serves as an anode 842. Under application of direct current, the negatively charged particles are drawn toward anode 842.

FIG. 8C shows probe 820 where side structural members serve as anode 842 while the core serves as cathode 826.

FIG. 8D shows another embodiment where the core 832 is not an electrode and side structural members serve as individual electrodes. Side structural members are each charged differently with one structural member serving as anode 826 and the other side structural member serving as cathode 832.

Figure 8E:
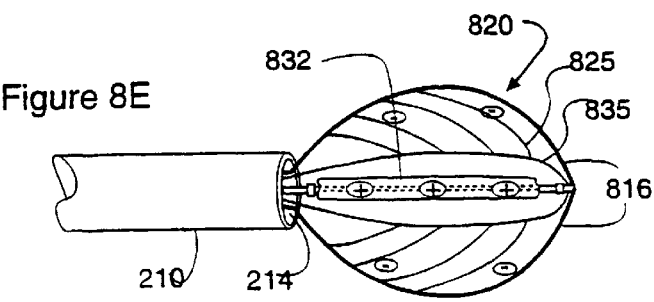

FIG. 8E shows an alternative embodiment of the functional aspect of probe 820 with additional intermediate side members 835. Intermediate side members 835 are, in a deployed state located radially between the core and an associated one the side members. Intermediate side members 835 are each electrically coupled to a corresponding one of side members 816 by means of electrical connectors/ ribs 825. The ribs create a greater electrical potential by increasing the electrode region. The individual ribs 825 may be constructed of the same material as intermediate side members 835 or any other electrically conductive material. The "fishrib" or fan-shaped structure of probe 820 in this embodiment creates a greater driving force for changing the chemical milieu of the intradiscal cavity by electrophoretic means.

Figure 8F:
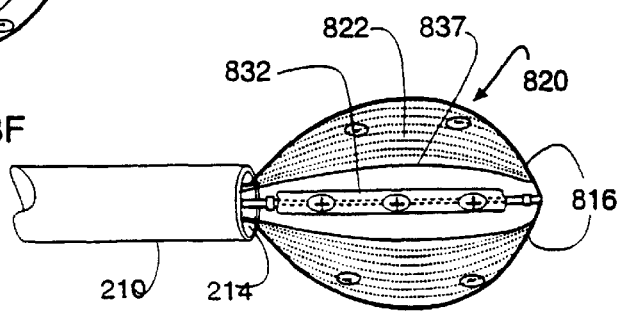

FIG. 8F is an embodiment whereby the greater electrical potential is created by increasing the surface area of the electrode region by use of a film 822 with an electrically conductive layer, e.g. vacuum metalized polyester. The conductive layer may be continuous or patterned. Opposing sides of the film are affixed to respective ones of intermediate side members 837 and side members 816. As the tip is deployed and expands to form an arcuate shape the film is deployed to expose the electrically conductive layer. The electrical gradient created is similar to FIG. 8E where a greater driving force pushes the negatively charged particles towards the central anode.

In another embodiment of the invention, the electrophoretic probe may be implemented utilizing a probe which, unlike the probes disclosed above, is substantially linear in shape. In this embodiment, electrophoretic functionality is achieved by axially displaced electrodes on the probe which are energized to opposing polarity to effect a migration of charged particles from one electrode to tie other, to achieve a beneficial therapeutic effect.

FIGS. 9A–D show the insertion stages of the catheter a surgical joint, in this case the intevertebral disc and specifically the nucleus pulposus 120 thereof. The device being inserted is the catheter 700 shown in FIG. 7.

Figure 9A:
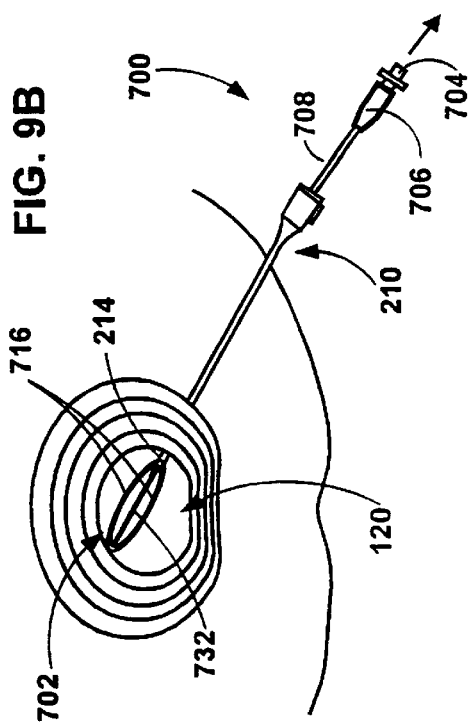
FIGS. 9A–D show the surgical steps connected with the insertion of the catheter of FIGS. 7–8 into a surgical site.

FIG. 9A shows the introducer 210 positioned so that the lumen at its distal end is within the intradiscal cavity. The stem 708 connects the handle 706 to the probe 702. The push-pull member 704 of the handle 706 is in the inserted position proximate to the handle. In that position the draw member 730 (not shown) is fully extended and the collapsible side members 716 lay flat against the axial core member 732 within the intradiscal cavity.

Figure 9B:
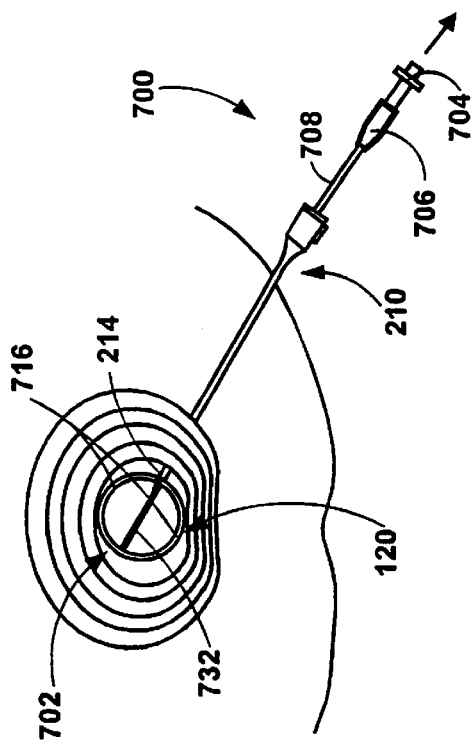
Figure 9C:
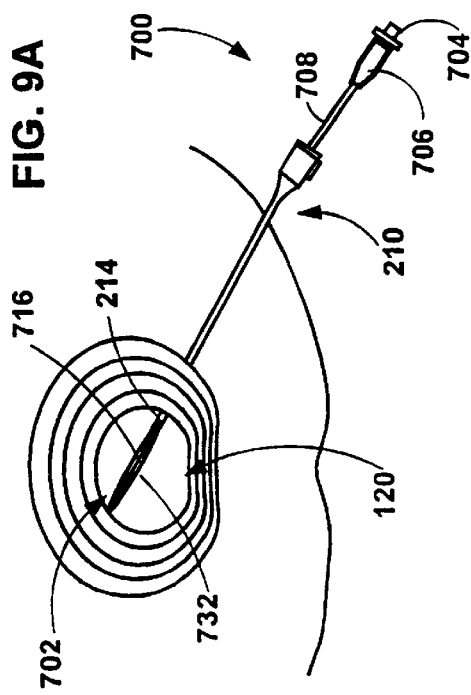
Figure 9D:
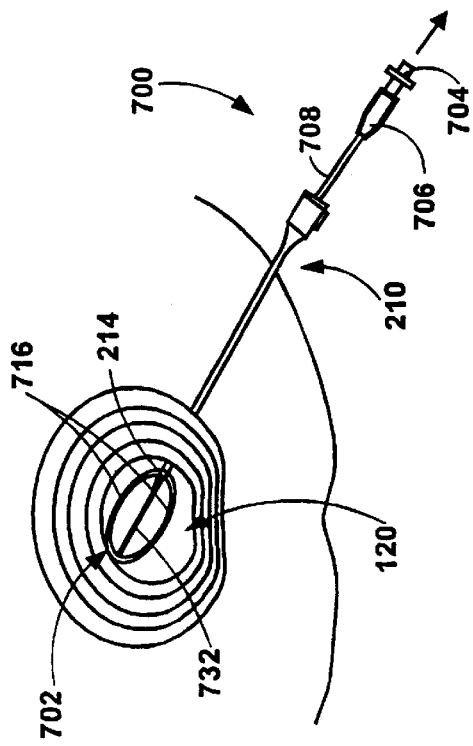

FIGS. 9B–D show various stages of the expansion of collapsible side members 716 radially about axial core member 732. This deployment is brought about by the retraction of the draw member 730 (not shown) through stem 708 by means of the displacement of the push-pull member 704 away from the handle 706.

Functional Elements

Since a purpose of the inventive catheter is to repair tears or fissures in a disc by operation of the instrument at the tear location adjacent to or inside the disc, a functional element is provided in or on the catheter to carry out that purpose.

Non-limiting examples of functional elements include any element capable of aiding diagnosis, delivering energy, or delivering or removing a material from a location adjacent the element's location in the catheter, such as an opening in the catheter for delivery of a fluid (e.g., dissolved collagen to seal the fissure) or for suction, a thermal energy delivery device (heat source), a mechanical grasping tool for removing or depositing a solid, a cutting tool (which includes all similar operations, such as puncturing), a sensor for measurement of a function (such as electrical resistance, temperature, or mechanical strength), or a functional element having a combination of these functions.

The functional element can be at varied locations in the probe portion of the catheter, depending on its intended use. Multiple functional elements can be present, such as multiple functional elements of different types (e.g., a heat source and a temperature sensor) or multiple functional elements of the same type (e.g., multiple heat sources spaced along the probe portion).

One of the possible functional elements present on probe section 216 is a thermal energy delivery device. A variety of different types of thermal energy can be delivered including but not limited to resistive heat, radio frequency (RF), coherent and incoherent light, microwave, ultrasound and liquid thermal jet energies. In one embodiment, thermal energy delivery device is positioned proximal to the distal portion of probe section 216 so that there is no substantial delivery of energy at the distal portion, which can then perform other functions without being constrained by being required to provide energy (or resist the resulting heat).

The energy directing device is configured to limit thermal and/or electromagnetic energy delivery to a selected site of the disc and to leave other sections of the disc substantially unaffected. The energy can be directed to the walls of the fissure to cauterize granulation tissue and to shrink the collagen component of the annulus, while the nucleus is shielded from excess heat.

In various embodiments, catheter probe section 216 and/ or tip 220 are positionable to selected site(s) around and/or adjacent to inner wall of an annulus fibrosus for the delivery of therapeutic and/or diagnostic agents including but not limited to, electromagnetic energy, electrolytic solutions, contrast media, pharmaceutical agents, disinfectants, collagens, cements, chemonucleolytic agents and thermal energy. Probe section 216 is navigational and can reach the posterior, the posterior lateral, the posterior medial, anterior lateral, and anterior medial regions of the annulus fibrosus, as well as selected section(s) on or adjacent to inner wall of the nucleus pulposus 120.

In FIGS. 10A–B, 11, 12A–C embodiment of the catheter are shown in which the probe delivers thermal energy to reduce pain without ablation or removal of any disc adjacent to and with or without removal of water vapor from the disc but without charring the nucleus. The probe section also can heat the collagen components of the annulus, thereby shrinking the annulus, with or without desiccating local tissue.

Figure 10A:
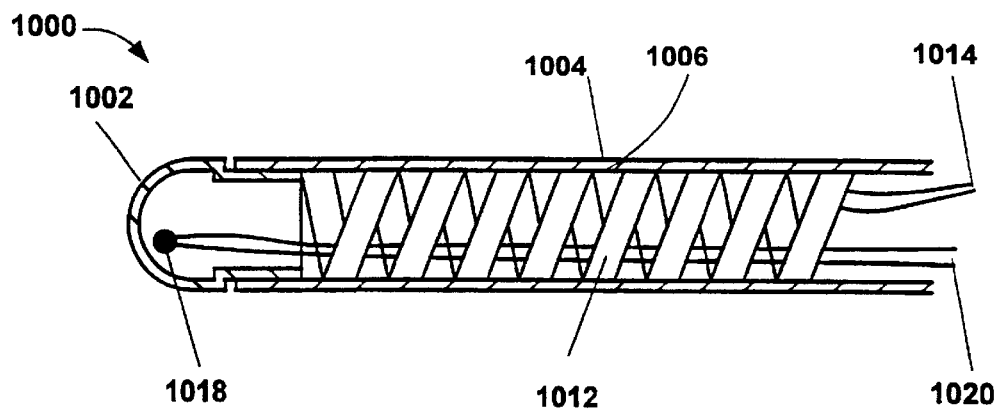
FIGS. 10A–B show catheters with thermal energy delivery sources.
Figure 10B:
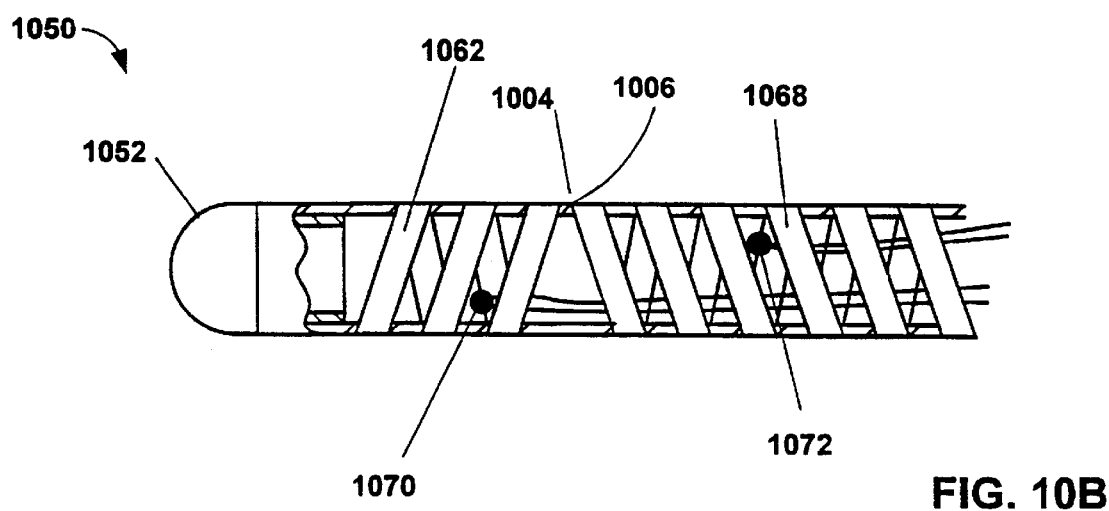

FIGS. 10A–B show alternate embodiments of a probe and tip, which include a functional elements with the capability of delivering energy to the surgical site. In FIG. 10A, the functional elements exhibits combined resistive and radio frequency energy delivery capability. In FIG. 10B, the device includes dual resistive heating capability.

In FIG. 10A, the distal portion of a probe 1000 is shown. The probe is tubular with an interior wall 1006. At the distal end of the probe a tip 1002 is affixed to the probe. Within the interior of the probe a resistive heating coil 1012 is positioned. The resistive heating coil is coupled via wires 1014 extending through the stem and handle to an energy delivery device 202 (see FIG. 2A). In the embodiment shown, the probe itself is electrically conductive, thus allowing for the delivery of R.F. power to tip 1002 at the terminus of the probe 1000. The tip in combination with a return pad (not shown) affixed to the patient, provides monopolar R.F. delivery to the surgical site. To prevent R.F. power emanating from the exterior of the probe, an outer sheath 1004, which is electrically insulating, is provided to surround all except the terminus of probe 1000. To measure the temperature at the tip, a temperature sensing device 1018 is positioned inside the tip. That device is coupled via wires 1020 which extend the length of the stem to the handle to external controls for monitoring energy to the surgical site. Heating coil 1012 may be powered by a direct current source (and less preferably a source of alternating current). Heating coil 1012 is made of a material that acts as a resistor. Suitable materials include but are not limited to stainless steel, nickel/chrome alloys, platinum, and the like. Preferably, the heating element is inside the probe. The resistive material is electrically insulated and substantially no current escapes into the body. With increasing levels of current, the coils heat to greater temperature levels. In one embodiment, 2 watts pass through heating element 46 to produce a temperature of about 55° C. in a selected target such as fissure, 3 watts produces 65° C., 4 watts produces 75° C., and so on.

FIG. 10B shows an alternate embodiment of the energy delivery element. In this embodiment dual resistive/radiofrequency heat delivery is provided. The probe 1050 defines an interior lumen portion in which tip 1052 is placed. A short and long heating element, respectively 1062–1068, are positioned around the exterior of the probe, and are electrically connected wires (not shown) to energy delivery device 202 (see FIG. 2A). To monitor the temperature of each of the coils thermo-couples 1070 and 1072 are provided.

In another embodiment, radio frequency energy is delivered to the heating elements. As illustrated in FIG. 10B coils 1062, 1068 are positioned on the exterior of probe 1050 and serve as RF electrodes powered by an RF generator. The electrodes are made of suitable materials including but not limited to stainless steel or platinum Increasing levels of current conducted into disc tissue heat that tissue to greater temperature levels. A circuit can be completed substantially entirely at probe section 16 (bipolar device) or by use of a second electrode attached to another portion of the patient's body (monopolar device). In either case, a controllable delivery of RF energy is achieved.

In another embodiment sufficient energy is delivered to the intervertebral disc to heat and shrink the collagen component of the annulus but not ablate tissue adjacent to catheter 14. With a resistive heating device, the amount of thermal energy delivered to the tissue is a function of (i) the amount of current passing through heating element, (ii) the length, shape, and/or size of the heating element, (iii) the resistive properties of the heating element, (iv) the gauge of heating element, and (v) the use of cooling fluid to control temperature. All of these factors can be varied individually or in combination to provide the desired level of heat. Energy delivery device 202 associated with the heating element may be battery based. The catheters can be sterilized and may be disposable.

Figure 11:
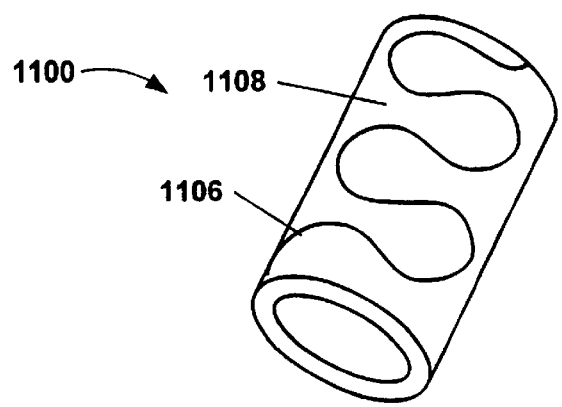
FIG. 11 shows a thermal delivery element for a catheter.

FIG. 11 shows an alternate embodiment for the construction of resistive heating coils. In the embodiment shown, a thin film resistive element, generally 1100, fabricated using technology derived from printed circuit boards, is provided. In this embodiment, the resistive wire 1106 is fabricated as part of a substrate or film 1108, using photoetch/engraving techniques. The substrate might for example be a polyester film. The wire may be internal to or deposited on a surface of the substrate. The coil can be fabricated on one side only of the substrate of film 1108, thus allowing for asymmetric delivery of heat. In assembly, the core can be positioned in the interior of the probe or heat shrunk around the exterior of the probe.

Figure 12A:
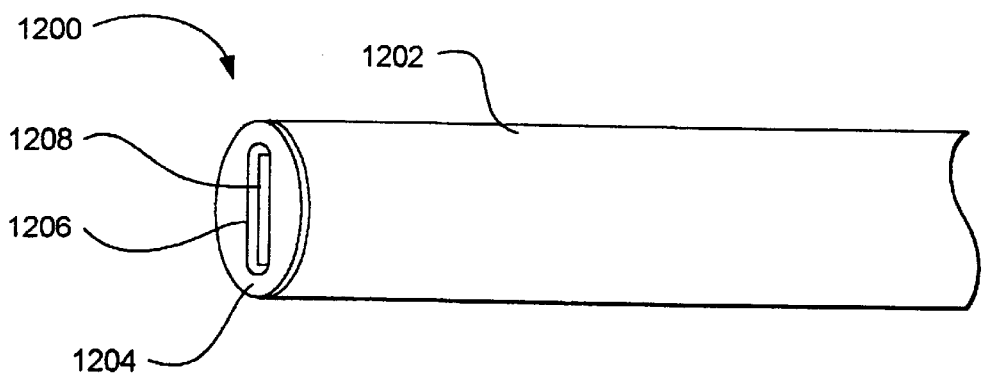
FIGS. 12A–C show a catheter probe with a knife, lumen, and energy delivery element.
Figure 12B:
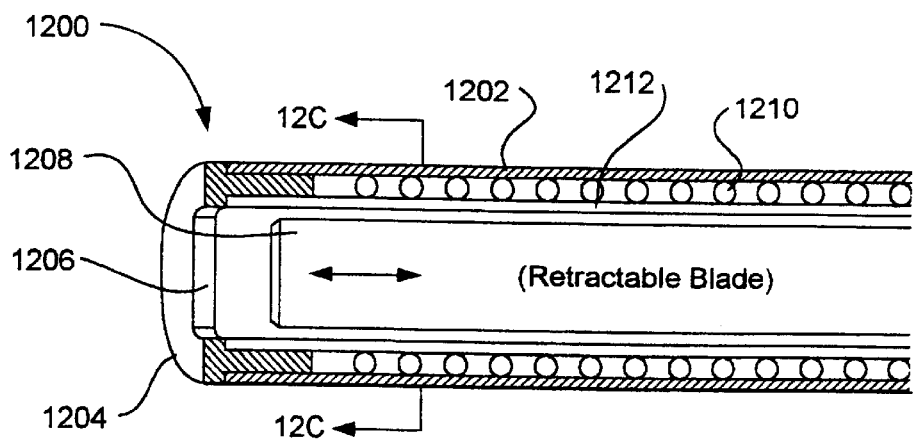
Figure 12C:
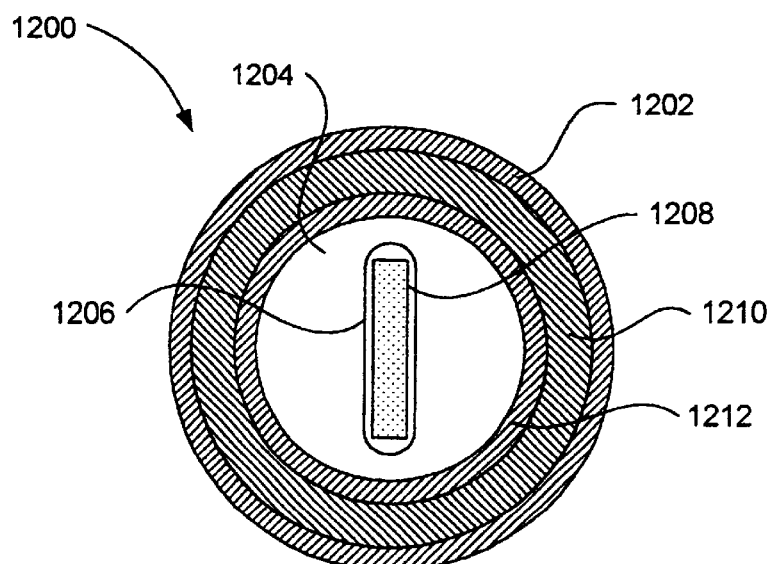

FIGS. 12A–C show an alternate embodiment of the invention in which a number of functional elements are provided, including a retractable blade, a lumen and a resistive heating element. FIG. 12A shows an exterior side view of probe 1200. FIG. 12B shows a side view of the probe 1200. FIG. 12C shows a cross-sectional axial view from the probe interior facing the tip end of the probe.

FIG. 12A shows the probe 1200, generally tubular in shape, with an exterior tubular portion 1202. At the distal end of the probe a tip 1204 is affixed. The tip defines in its face, a lumen 1206 in which the cutting tip of a retractable blade 1208 is shown in the retracted position. In an embodiment of the invention, the exterior dimensions of the retractable blade are sufficiently less that the interior dimensions of the lumen 1206 so as to allow for not only the retraction and extension of the blade, but also for either the removal by suction or introduction by pressure of material from or to the surgical site.

FIG. 12B shows the cross-sectional view of the probe shown in FIG. 12A. In addition to the features discussed above, the device is seen to include resistive heating coils 1210 contained within a spacing between the exterior tubular portion 1202 and an interior tubular portion 1212 of the probe 1200. The retractable blade is in turn slidably positioned within the interior tubular portion.

FIG. 12C shows a cross-sectional view facing toward the end of probe 1200. The exterior tubular portion 1202 and the interior tubular portion 1212 of the probe 1200 are shown. In the spacing between them the resistive heating coils 1210 are shown. The blade 1208 is axially positioned within the inner tubular wall 1212.

The lumen 1206 may be configured to transport a variety of different mediums including but not limited to electrolytic solutions (such as normal saline), contrast media (such as Conray meglumine iothalamate), pharmaceutical agents, disinfectants, filling or binding materials such as collagens or cements, chemonucleolytic agents and the like, from the material delivery/removal device 204 (see FIG. 2A) to a desired location within the interior of a disc (i.e., the fissure). Further, the lumen can be used to remove nucleus material or excess liquid or gas (naturally present, present as the result of a liquefying operation, or present because of prior introduction) from the interior of a disc. When used to transport a fluid for irrigation of the location within the disc where some action is taking place (such as ablation, which generates waste materials), the lumen is sometimes referred to as an irrigation lumen. The lumen can be coupled to the material delivery/removal device 204 through the catheter. In addition to or in substitution for the cutting blade, other instruments can be delivered through the lumen including but not limited to: graspers, drill and biopsy needle.

Figure 13:
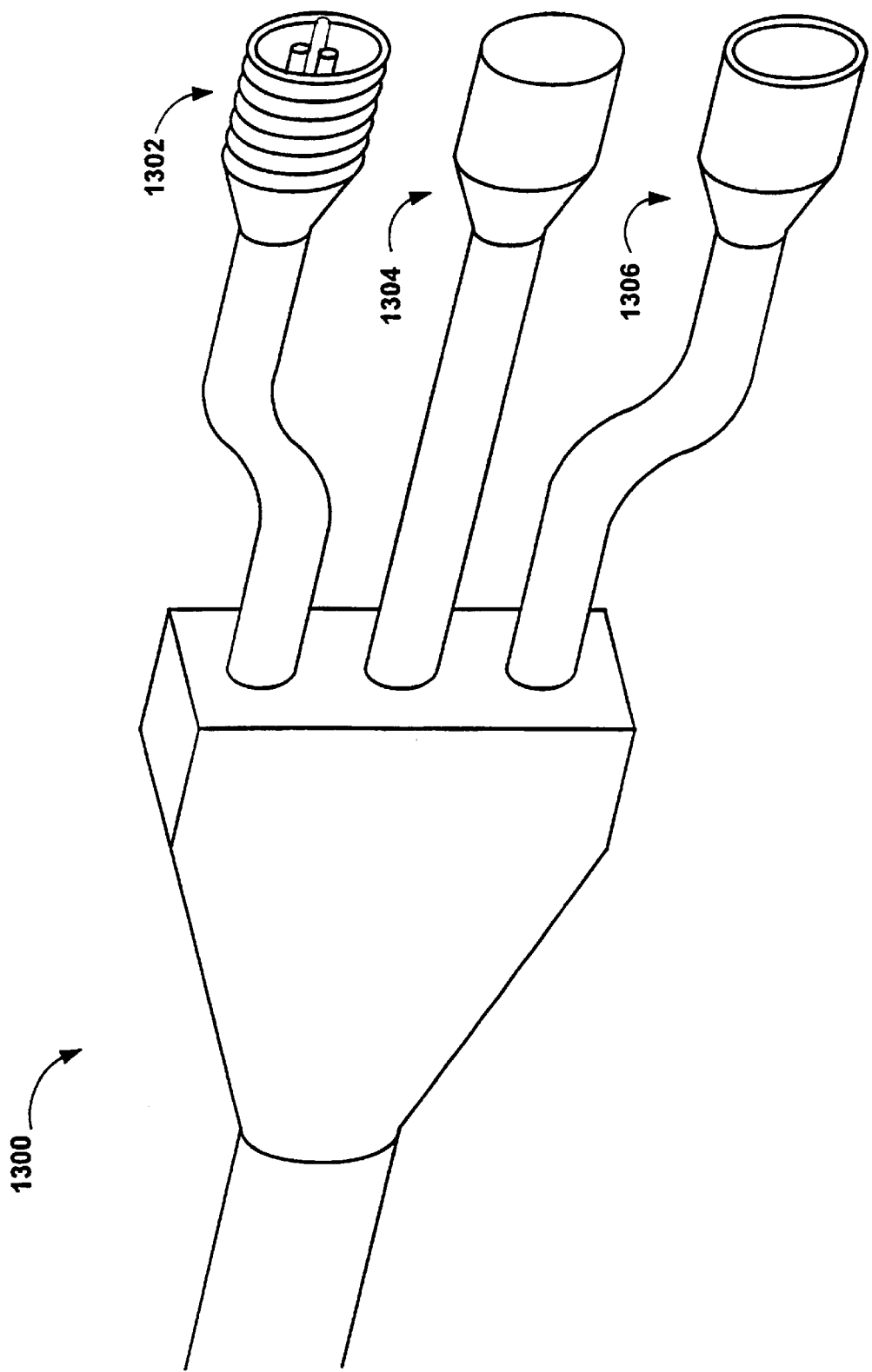
FIG. 13 shows a catheter connector including fluid delivery coupling.

FIG. 13 shows a split interface generally 1300 for providing connections on the handle of the catheter to join energy delivery and material transfer elements within the probe 216 (See FIG. 2A) of the catheter to material delivery/removal device 204 and energy delivery device 202 (see FIG. 2A). An electrical interface 1302, a luer interface 1306 for fluids and an auxiliary interface 1304 are shown. The auxiliary interface could be utilized for a needle syringe, graspers or an optical fiber for viewing a surgical site. As will be obvious to those skilled in the art, the probe may be configured for any one or all of these functional elements.

Figure 14:
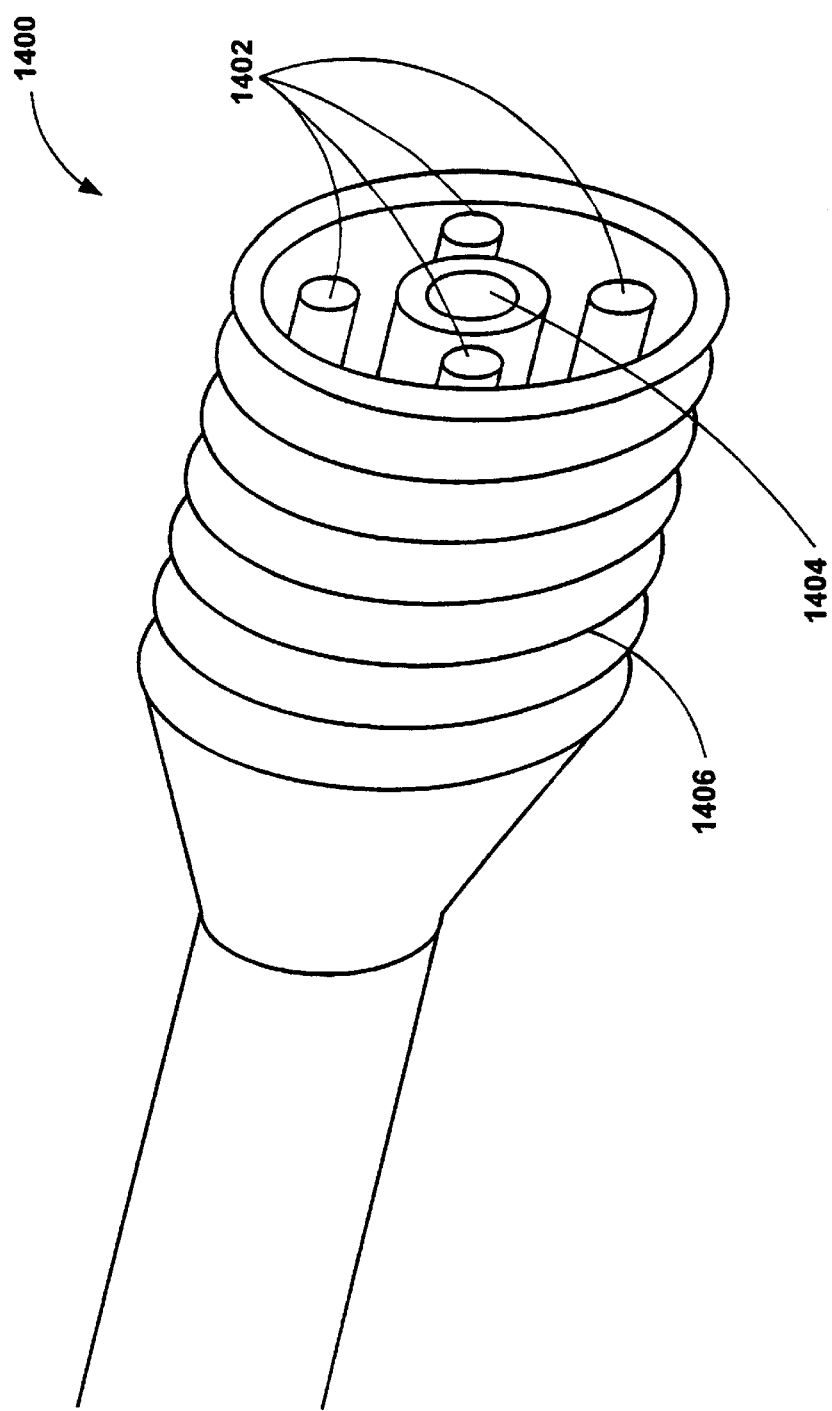
FIG. 14 shows another connector with fluid delivery coupling.

FIG. 14 shows an integrated interface 1400 for providing connections on the handle of the catheter to join energy delivery and material transfer elements within the probe 216 (See FIG. 2A) of the catheter to material delivery/removal device 204 and energy delivery device 202 (see FIG. 2A). Electrical interfaces generally 1402 and a luer interface 1404 for the introduction or removal of material to the surgical site are shown. External threads 1406 are shown for coupling the interface to material and energy delivery devices.

All publications, patent applications, and issued patents mentioned in this application are hereby incorporated herein by reference in their entirety to the same extent as if each individual publication, application, or patent was specifically and individually indicated to be incorporated in its entirety by reference.

All the disclosed embodiments of the invention described herein can be realized and practiced without undue experimentation. Although the best mode of carrying out the invention contemplated by the inventors is disclosed above, practice of the present invention is not limited thereto. Accordingly, it will be appreciated by those skilled in the art that the invention may be practiced otherwise than as specifically described herein.

For example, the individual components need not be formed in the disclosed shapes, or assembled in the disclosed configuration, but could be provided in virtually any shape, and assembled in virtually any configuration. Further, the individual components need not be fabricated from the disclosed materials, but could be fabricated from virtually any suitable materials. Furthermore, all the disclosed elements and features of each disclosed embodiment can be combined with, or substituted for, the disclosed elements and features of every other disclosed embodiment except where such elements or features are mutually exclusive.

It will be manifest that various additions, modifications and rearrangements of the features of the present invention may be made without deviating from the spirit and scope of the underlying inventive concept. It is intended that the scope of the invention as defined by the appended claims and their equivalents cover all such additions, modifications, and rearrangements. The appended claims are not to be interpreted as including means-plus-function limitations, unless such a limitation is explicitly recited in a given claim using the phrase "means for." Expedient embodiments of the invention are differentiated by the appended subclaims.

What is claimed is:

1. A device for delivering energy to an intervertebral disc comprising:
   a catheter consisting of a single elongated unitary body, the catheter comprising
      a handle at a proximal end of the catheter and a probe at a distal end of the catheter,
      at least one energy delivery device located at the distal end of the catheter to deliver energy to portions of the intervertebral disc, and
      an activation element located at the distal end of the catheter which predisposes the catheter body to adopt an arcuate shape within the intervertebral disc.

2. The device of claim 1, wherein the activation element comprises:
   a resilient material which in a relaxed state effects an arcuate shape and which upon introduction of external stress assumes a substantially linear shape.

3. The device of claim 2, further comprising:
   an introducer defining along a longitudinal axis a lumen dimensioned to apply external stress to the resilient material.

4. The device of claim 1, wherein the activation element comprises:
   at least two materials exhibiting differential coefficients of thermal expansion and the at least two materials joined to one another wherein at a first temperature the at least two materials assume a substantially linear shape and at a second temperature the at least two materials assume an arcuate shape.

5. The device of claim 1, wherein the activation element comprises:
   a material with a temperature dependent shape memory wherein at a first temperature the material assumes a substantially linear shape and at a second temperature the material assumes an arcuate shape.

6. The device of claim 5, wherein the material comprises nickel-titanium.

7. The device of claim 1, wherein the activation element comprises:
   a mandrel with a longitudinal axis, and the mandrel including a differential bending ability in two orthogonal axis which are orthogonal to the longitudinal axis; and
   a tension member joined to the mandrel at a distal end thereof, and coextensive with the longitudinal axis of the mandrel along a length thereof, and the mandrel responsive to tension applied to the tension member, to effect a transition of the mandrel from a substantially linear shape to an arcuate shape.

8. The device of claim 1, wherein the activation element comprises:
   at least two side members extending axially along a longitudinal axis of the probe and rigidly affixed at first ends thereof to the probe, and the at least two side members moveable from a first position proximate to the longitudinal axis of the probe to a second position radially displaced about the longitudinal axis of the probe.

9. The device of claim 8, wherein the at least two side members comprise:

a resilient material which in a relaxed state effects an arcuate shape and which upon introduction of external stress assumes a substantially linear shape.

10. The device of claim 9, further comprising:

an introducer defining along a longitudinal axis a lumen dimensioned to apply external stress to the resilient material.

11. The device of claim 8, wherein the at least two side members comprise:

at least two materials exhibiting differential coefficients of thermal expansion and at least two materials joined to one another wherein at a first temperature the at least two materials assume a substantially linear shape and at a second temperature the at least two materials assume an arcuate shape.

12. The device of claim 8, wherein the at least two side members comprise:

a material with a temperature dependent shape memory wherein at a first temperature the material assumes a substantially linear shape and at a second temperature the material assumes an arcuate shape adapted to abut at least a portion of the inner wall of.

13. The device of claim 12, wherein the material comprises nickel-titanium.

14. The device of claim 8, wherein the at least two side members comprise;

a resilient material which in a relaxed state effects a linear shape and which upon introduction of a compressive force between the first ends of the at least two side members and second ends thereof assumes a substantially arcuate shape; and a draw member coupled to the handle for applying the compressive force to the resilient material, to effect a transition of the at least two side members from a substantially linear shape to an arcuate shape.

15. The device of claim 14, wherein the energy delivery element further comprises;

a core parallel to the longitudinal axis of the probe; and electrical couplings for applying electrical power of an opposing polarity to respectively said at least two side members and said core.

16. The device of claim 1, wherein the energy delivery element further comprises;

at least one resistive coil located within the probe at a distal end thereof; and electrical couplings for applying electrical power to said at least one resistive coil.

17. The device of claim 1, wherein the energy delivery element includes a thermal energy delivery element.

18. The device of claim 17, wherein said thermal energy delivery element comprises at least one of a resistive heating element and at least one radio frequency electrode.

19. The device of claim 17, wherein the thermal energy delivery element comprises:

a substrate fastened to the distal end of the catheter; and a heating element fabricated on said substrate by a photo-etching.

20. A catheter for delivering energy to an intervertebral disc, and said catheter including at a proximal end a handle and at a distal end a probe and said intervertebral disc having a nucleus pulposus, an annulus fibrosus, and an inner wall of said annulus fibrosus, said nucleus pulposus having a first diameter in a disc plane between opposing sections of said inner wall, and said catheter comprising:

at least one energy delivery device located at the distal end of the catheter to deliver energy to portions of the intervertebral disc; and an activation element located at the distal end of the catheter, to transition the probe from a linear to a multi-dimensional shape, within the intervertebral disc, wherein the activation element comprises:

a mandrel with a longitudinal axis, and the mandrel including a differential bending ability in two orthogonal axis which are orthogonal to the longitudinal axis; and a piezo-electric material joined to the mandrel along a length thereof, and the piezoelectric material responsive to an electrical stimulus to vary at least one dimension thereof, to effect a transition of the mandrel from a substantially linear shape to an arcuate shape.

* * * * *

UNITED STATES PATENT AND TRADEMARK OFFICE
CERTIFICATE OF CORRECTION

PATENT NO. : 6,258,086 B1
DATED : July 10, 2001
INVENTOR(S) : John E. Ashley et al.

It is certified that error appears in the above-identified patent and that said Letters Patent is hereby corrected as shown below:

<u>Title page,</u>
Item [60], delete "provisional application No. 08/881,525, filed on Oct. 23, 1996, provisional application No. 08/881,692, filed on Oct. 23, 1996, provisional application No. 08/881,693, filed on Oct. 23, 1996, provisional application No. 08/881,694, filed on October 23, 1996,"

<u>Column 24,</u>
Lines 7-18, should read as follows:

1. A device for delivering energy to an intervertebral disc comprising:
 a catheter consisting of a single elongated
unitary body, the catheter comprising
 a handle at a proximal end of the catheter
and a probe at a distal end of the catheter,
 at least one energy delivery device located
at the distal end of the catheter to deliver energy to
portions of the intervertebral disc, and
 an activation element located at the distal
end of the catheter which predisposes the catheter body
to adopt an arcuate shape adapted to abut at least a
portion of the inner wall of the intervertebral disc.

Signed and Sealed this

Eighteenth Day of March, 2003

JAMES E. ROGAN
*Director of the United States Patent and Trademark Office*